(12) United States Patent
Warisawa et al.

(10) Patent No.: US 12,218,513 B2
(45) Date of Patent: Feb. 4, 2025

(54) POWER TRANSFER SYSTEM, POWER TRANSFER DEVICE, POWER RECEPTION DEVICE, AND WIRELESS POWER TRANSFER METHOD

(71) Applicant: THE UNIVERSITY OF TOKYO, Tokyo (JP)

(72) Inventors: Shinichi Warisawa, Tokyo (JP); Yen Po Wang, Tokyo (JP); Munemasa Sugimoto, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 25 days.

(21) Appl. No.: 18/042,549

(22) PCT Filed: Oct. 13, 2021

(86) PCT No.: PCT/JP2021/037965
§ 371 (c)(1),
(2) Date: Feb. 22, 2023

(87) PCT Pub. No.: WO2022/080434
PCT Pub. Date: Apr. 21, 2022

(65) Prior Publication Data
US 2023/0344273 A1    Oct. 26, 2023

(30) Foreign Application Priority Data
Oct. 16, 2020    (JP) ................. 2020-174904

(51) Int. Cl.
*H02J 50/05*    (2016.01)
*H02J 50/80*    (2016.01)

(52) U.S. Cl.
CPC .............. *H02J 50/05* (2016.02); *H02J 50/80* (2016.02)

(58) Field of Classification Search
CPC ....................................................... H02J 50/05
See application file for complete search history.

(56) References Cited

U.S. PATENT DOCUMENTS 10,128,660 B1    11/2018 Apte et al.
10,355,536 B1 *  7/2019  Grundmann ............ H02J 50/90
(Continued)

FOREIGN PATENT DOCUMENTS

CN    112701800 A  *  4/2021  ............. H02J 50/05
JP    H07-265442 A    10/1995
(Continued)

OTHER PUBLICATIONS

H. Zheng, K. Tnay, N. Alami, and A. P. Hu, "Contactless Power Couplers for Respiratory Devices", presented at the Mechatronics and Embedded Systems and Applications (MESA), 2010 IEEE/ASME International Conference on, 2010, 6 pages.
(Continued)

*Primary Examiner* — Ryan Johnson
(74) *Attorney, Agent, or Firm* — Merchant & Gould P.C.

(57) ABSTRACT

A power transfer device including an AC power source unit and a single power transfer element, and a power reception device including a single power reception element electrically coupled to the power transfer element and a power reception circuit outputting power are included. The power reception circuit includes a different potential field disposed at a position that is an electric field formed by the power transfer element and at which intensity of the electric field is different from intensity of an electric field formed at a position of the power reception element.

21 Claims, 19 Drawing Sheets

(56) References Cited

U.S. PATENT DOCUMENTS

2013/0264886 A1    10/2013  Nakatani et al.
2015/0333539 A1*   11/2015  Kusunoki ............... H02J 50/12
                                                    307/104

FOREIGN PATENT DOCUMENTS

| JP | 2013-219888 A | 10/2013 |
| JP | 2019-161929 A | 9/2019 |
| JP | 2019-161937 A | 9/2019 |

OTHER PUBLICATIONS

International Search Report for the corresponding Patent Application No. PCT/JP2021/037965 dated Dec. 21, 2021, with English translation.
European Patent Office, "Extended European Search Report" dated Jul. 2, 2024 in connection with the related European patent application No. 21880171.0, 9 pages.

* cited by examiner

------- : POTENTIAL FIELD

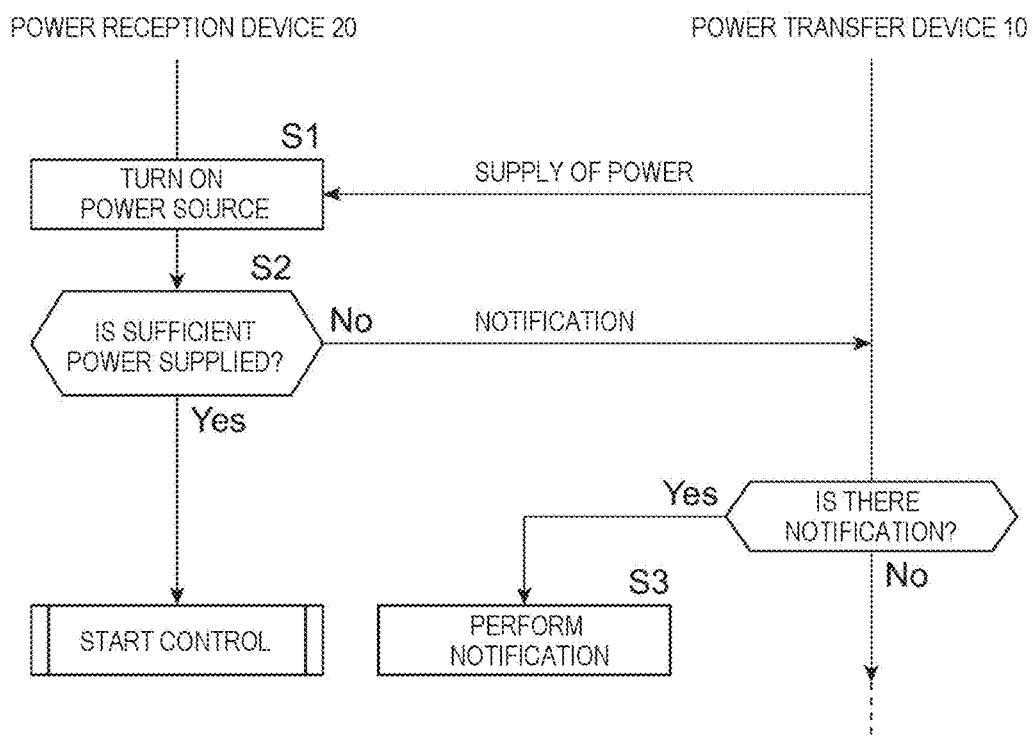

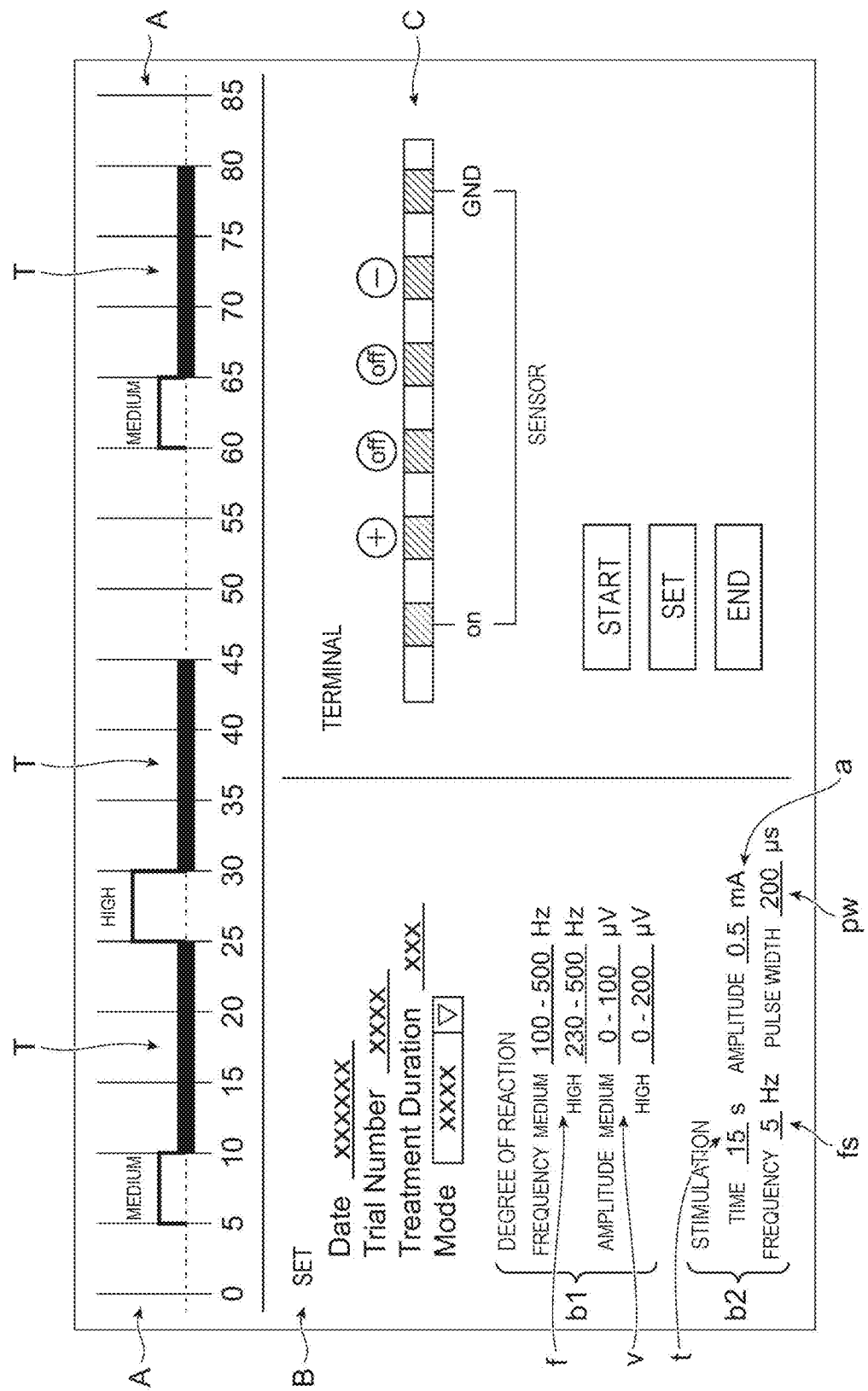

POWER TRANSFER SYSTEM, POWER TRANSFER DEVICE, POWER RECEPTION DEVICE, AND WIRELESS POWER TRANSFER METHOD

CROSS REFERENCE TO RELATED APPLICATION

This Application is a 371 of PCT/JP2021/037965 filed on Oct. 13, 2021 which, in turn, claimed the priority of Japanese Patent Application No. 2020-174904 filed on Oct. 16, 2020, both applications are incorporated herein by reference.

TECHNICAL FIELD

The present invention relates to a power transfer system that wirelessly transfers power, a power transfer device, a power reception device, and a wireless power transfer method.

BACKGROUND ART

The wireless power transfer method is roughly divided into a method using inductive coupling (Inductive Power Transfer (IPT)) and a method using capacitive coupling (Capacitive Power Transfer (CPT)). In the method using inductive coupling, relatively high power can be transferred, but there are problems that power transfer efficiency greatly changes depending on alignment between the power transfer device and the power reception device, and a heat generation amount of a circuit is great.

On the other hand, in the method using capacitive coupling, an amount of power that can be transferred is generally smaller than that in the method using inductive coupling, but a change in power transfer efficiency depending on alignment between the power transfer device and the power reception device is relatively small, and the heat generation amount of the circuit during power transfer is also smaller than that in the method using inductive coupling.

As described above, the power transfer using the inductive coupling and the power transfer using the capacitive coupling have advantages and disadvantages, and any power transfer method is currently adopted according to the use.

Specifically, as a method of wirelessly supplying power to a cardiac pacemaker embedded in a human body, a nerve stimulation device, various signal detection devices, and the like, a method using capacitive coupling in which a heat generation amount of a circuit during power transfer is relatively small is suitable.

An example of a power transfer system using capacitive coupling in the related art is illustrated in FIG. 22. As illustrated in FIG. 22, in the power transfer system in the related art, a power transfer device 100 and a power reception device 200 includes a pair of plates 101 and 102, and a pair of plates 201 and 202, respectively. In the power reception device 200, a load 210 is disposed between the plates 201 and 202. Furthermore, in the power transfer device 100, a ground terminal GND of a power source 110 is connected to the plate 102 side, and the ground terminal GND is connected to a common potential point (for example, grounded). Moreover, a power supply side terminal of the power source 110 is connected to the plate 101.

In this example of the related art, power transferred to a load 210 by capacitive coupling between the plate 101 and the plate 201 "returns" to the ground terminal GND of the power transfer device 100 by capacitive coupling between the plate 202 and the plate 102, and thus a current flows through the load 210 (for example, Non-Patent Literature 1).

CITATION LIST

Non-Patent Literature

Non-Patent Literature 1: H. Zheng, K. Tnay, N. Alami, and A. P. Hu, "Contactless Power Couplers for Respiratory Devices", presented at the Mechatronics and Embedded Systems and Applications (MESA), 2010 IEEE/ASME International Conference on, 2010.

SUMMARY OF INVENTION

Technical Problem

However, in the power transfer method using capacitive coupling of the related art, it is necessary to prepare two pairs of plates, and it may be difficult to dispose the plates according to the use. Furthermore, it is necessary to capacitively couple pairs of the plates, and there is a problem that alignment of the plates is difficult according to the use.

The present invention has been made in view of the above circumstances, and an object of the present invention is to provide a power transfer system capable of transferring power by using a pair of plates and improving the efficiency thereof, a power transfer device, a power reception device, and a wireless power transfer method.

Solution to Problem

In order to solve the problem in the related art, according to an aspect of the present invention, there is provided a power transfer system including a power transfer device and a power reception device which wirelessly transmit and receive power, respectively, in which the power transfer device includes an AC power source unit, and a single power transfer element connected to the AC power source unit, the power reception device includes a single power reception element electrically coupled to the power transfer element of the power transfer device, and a power reception circuit connected to the power reception element and outputting power, and the power reception circuit includes a different potential field that is disposed at a position that is an electric field formed by the power transfer element and at which intensity of the electric field is different from intensity of an electric field formed at a position of the power reception element.

Advantageous Effect of Invention

According to the present invention, the power can be transferred by a pair of plate-shaped or coil-shaped conductive elements, and the efficiency thereof can be improved.

BRIEF DESCRIPTION OF DRAWINGS

FIG. 16 is a flowchart illustrating an operation example of a power transfer system according to the embodiment of the present invention.

FIG. 19 is an explanatory diagram illustrating an example of a screen for performing setting for a power transfer system according to the embodiment of the present invention.

DESCRIPTION OF EMBODIMENTS

Figure 1:
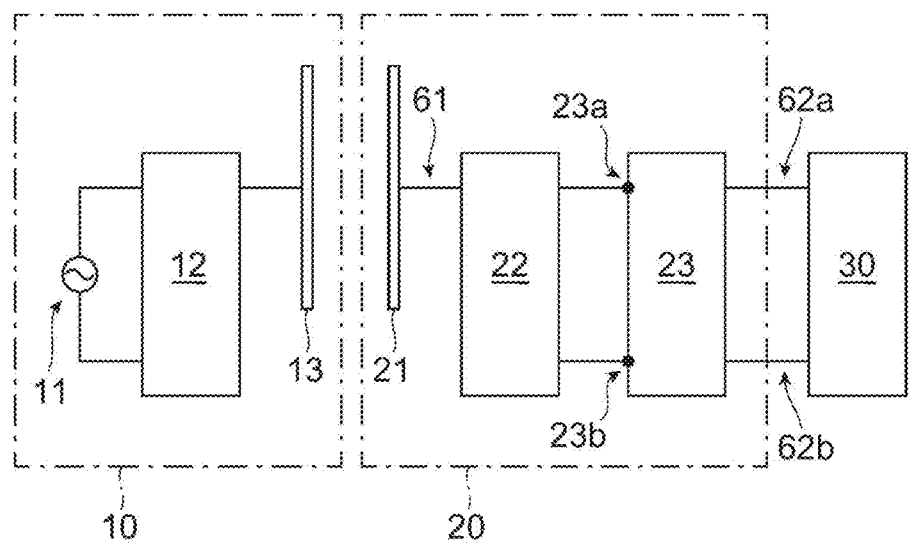
FIG. 1 is a block diagram illustrating a schematic configuration of a power transfer system according to an embodiment of the present invention.

An embodiment of the present invention will be described with reference to the drawings. Note that in the following description, the sizes and ratios of the units are merely examples, and the examples of the present embodiment are not limited to the sizes and ratios illustrated in the drawings.

As schematically illustrated in FIG. 1, a power transfer system 1 according to the embodiment of the present invention includes a power transfer device 10 and a power reception device 20, and a load 30 is connected to the power reception device 20 via wirings 62$a$ and 62$b$.

The power transfer device 10 includes an AC power source unit 11, a power transfer-side compensation circuit 12, and a power transfer plate 13 as a single power transfer element. Furthermore, the power reception device 20 basically includes a power reception plate 21 as a single power reception element, a power reception-side compensation circuit 22, and an output circuit 23.

Here, the AC power source unit 11 of the power transfer device 10 operates as an AC power source of a predetermined frequency. In an example of the present embodiment, the AC power source unit 11 includes a DC power source and an class-E switching inverter. Such an example of the AC power source unit 11 is widely known, and thus a detailed description thereof will be omitted.

Figure 2A:
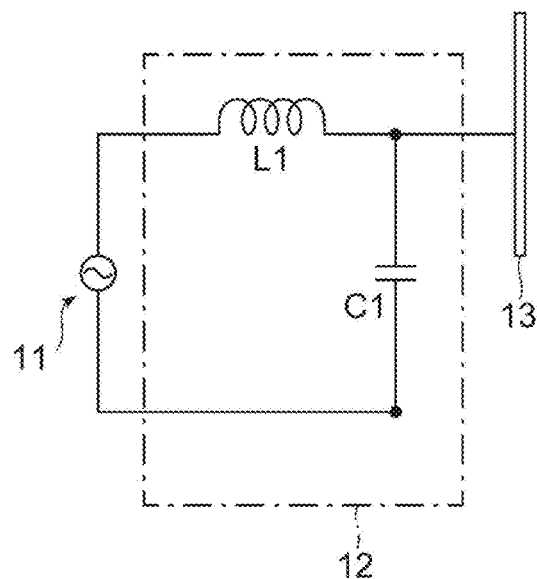
FIGS. 2A and 2B are schematic circuit diagrams illustrating an example of a power transfer-side compensation circuit of a power transfer device according to the embodiment of the present invention.

For example, as illustrated in FIG. 2A, the power transfer-side compensation circuit 12 includes a coil L1 and a capacitor C1, and one end of the coil L1 is connected to one end of an output terminal of the AC power source unit 11. Furthermore, the other end of the coil L1 is connected to one end of the capacitor C1, and is connected to the power transfer plate 13. The other end of the capacitor C1 is connected to the other end of the output terminal of the AC power source unit 11.

The power transfer plate 13 and the power reception plate 21 of the power reception device 20 are disposed to be opposed to each other. That is, with the power transfer plate 13 as a bottom surface, at least a part of the power reception plate 21 is included in a columnar movement trajectory (hereinafter, this region is referred to as an overlap region) obtained by virtually moving the bottom surface in a normal direction of the power transfer plate 13.

The power transfer plate 13 and the power reception plate 21 are capacitively coupled to each other when power is supplied from the AC power source unit 11. When the power transfer plate 13 and the power reception plate 21 are disposed, the centers of the power transfer plate 13 and the power reception plate 21 may not necessarily have to coincide with each other, and as will be described later, as long as there is an opposing portion (that is, as long as at least a part of the power reception plate 21 is included in the overlap region), the alignment between the centers may have a certain degree of deviation. Furthermore, the power transfer plate 13 and the power reception plate 21 may not necessarily need to be disposed strictly in parallel as long as the power transfer plate 13 and the power reception plate 21 can be capacitively coupled to each other.

Furthermore, the power transfer plate 13 and the power reception plate 21 have rectangular shapes with the same size in the drawing, but the power transfer plate 13 and the power reception plate 21 may have different sizes, or the power transfer plate 13 and the power reception plate 21 may have different shapes such as a length and width ratio. Moreover, both the power transfer plate 13 and the power reception plate 21 do not need to have a rectangular shape, and various shapes such as a rounded rectangle and an elliptical shape can be adopted depending on the use.

Figure 3A:
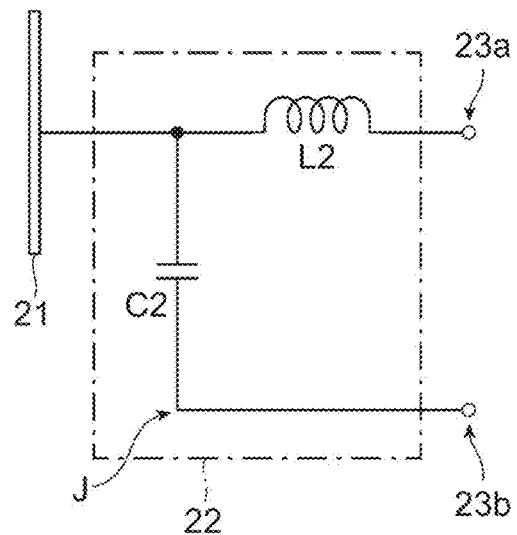
FIGS. 3A and 3B are schematic circuit diagrams illustrating an example of a power reception-side compensation circuit of a power reception device according to the embodiment of the present invention.

As illustrated in FIG. 3A, the power reception-side compensation circuit 22 includes a coil L2 and a capacitor C2. One end of the coil L2 is connected to the power reception plate 21, and is connected to one end of the capacitor C2 via a wiring 61. Furthermore, the other end of the coil L2 is connected to a first terminal 23a of the output circuit 23. The other end of the capacitor C2 is connected to a second terminal 23b of the output circuit 23.

In the example of the present embodiment, the output circuit 23 includes the first terminal 23a and the second terminal 23b, and the load 30 is connected between these terminals via wirings 62a and 62b. Furthermore, in this example, the other end of the capacitor C2 of the power reception-side compensation circuit 22 is disposed to be separated from the power reception plate 21. Specifically, the other end of the capacitor C2 is disposed at a position at which a distance Dr between the other end of the capacitor C2 and the power transfer plate 13 is greater than a distance Dp between the power transfer plate 13 and the power reception plate 21 by a predetermined distance d or more (position at which Dr≥Dp+d).

Figure 4:
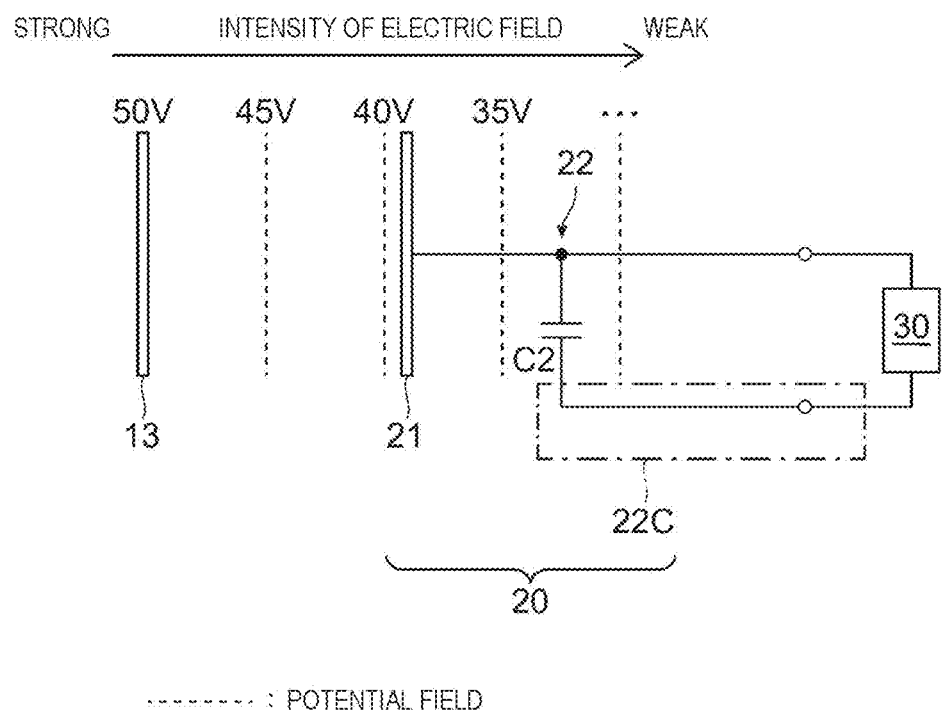
FIG. 4 is an explanatory diagram illustrating an electric field formed by a power transfer plate and an arrangement example of each unit of a power reception device in a power transfer system according to the embodiment of the present invention.

In this example of the present embodiment, the power transfer plate 13 generates an electric field (AC electric field) through the power transfer-side compensation circuit 12 with a current supplied from the AC power source unit 11. The intensity of the electric field changes depending on the distance from the power transfer plate 13 as illustrated in FIG. 4, and the intensity of the electric field decreases as the distance from the power transfer plate 13 increases. FIG. 4 is an explanatory diagram illustrating a schematic example of the arrangement of the power transfer system 1 of the present embodiment, an electric field formed by the power transfer plate 13 in the overlap region, and a potential field at a certain time point, which is formed by the electric field.

In an example of FIG. 4, in the vicinity of the power transfer plate 13, the electric field formed by the power transfer plate 13 has a direction substantially perpendicular to the power transfer plate 13. Therefore, the potential field formed based on the electric field is parallel to the power transfer plate 13 in the vicinity of the power transfer plate 13, and the magnitude of the potential at each potential field varies with time, but the potential decreases as the potential field moves away from the power transfer plate 13.

As described above, in the example of the present embodiment, the other end side 22C of the capacitor C2 of the power reception-side compensation circuit 22 is disposed such that a distance from the power transfer plate 13 to the other end side (indicated by a reference numeral 22C in FIG. 4) of the capacitor C2 of the power reception-side compensation circuit 22 is greater than a distance from the power transfer plate 13 to the power reception plate 21. Furthermore, the other end side 22C of the capacitor C2 may be disposed such that at least a part of the other end side 22C of the capacitor C2 is included in the overlap region of the power transfer plate 13.

Accordingly, the power reception plate 21 and the other end side 22C of the capacitor C2 are disposed on the potential fields having different potentials, which are formed by the power transfer plate 13. That is, here, the other end side 22C of the capacitor C2 functions as a different potential field. Furthermore, since one end and the other end of the capacitor C2 are not electrically short-circuited, a difference is generated between the potential of the power reception plate 21 and the potential of the other end side 22C of the capacitor C2 of the power reception-side compensation circuit 22, and a current flows through the load 30 connected between these potentials. That is, in this example of the present embodiment, power is transferred from the power transfer device 10 to the power reception device 20 by the single power transfer plate 13 and the power reception plate 21.

Note that in the example of the present embodiment, the other end of the capacitor C2 is disposed at a position at which the distance Dr between the other end of the capacitor C2 and the power transfer plate 13 is greater than the distance Dp between the power transfer plate 13 and the power reception plate 21 by 10 mm or more as the predetermined distance d (position at which Dr≥Dp+d).

Furthermore, the configuration of the different potential field of the present embodiment is not limited to this example. Here, the other end of the capacitor C2 of the power reception-side compensation circuit 22 is disposed at a position greater than the distance Dp between the power transfer plate 13 and the power reception plate 21 by a predetermined distance d or more. However, the power reception-side compensation circuit 22 itself (the entire power reception-side compensation circuit 22) may be disposed at a position greater than the distance Dp between the power transfer plate 13 and the power reception plate 21 by the predetermined distance d or more. Furthermore, this position may be outside the overlap region of the power transfer plate 13, or may be within the overlap region of the power transfer plate 13.

In this example, since the power reception plate 21 and the power reception-side compensation circuit 22 are disposed on the potential fields having different potentials, which are formed by the power transfer plate 13, the potential moves between the power reception plate 21 and the power reception-side compensation circuit 22, and a current is generated. That is, in this example, the entire power reception-side compensation circuit 22 functions as a different potential field.

Moreover, in another example of the present embodiment, still another wiring (hereinafter, referred to as an extension wiring) may be connected to the other end (wiring J in FIG. 3 and a wiring 22C in FIG. 4) of the capacitor C2 of the power reception-side compensation circuit 22, and an end of the extension wiring may be disposed at a position greater than the distance Dp between the power transfer plate 13 and the power reception plate 21 by a predetermined distance d or more. Furthermore, this position may be outside the overlap region of the power transfer plate 13, or may be within the overlap region of the power transfer plate 13. Note that the end of the extension wiring may be an open end, or may be connected to another conductor, GND, another circuit configuration, or the like as long as it is not short-circuited to one end of the capacitor C2. In this example, the end of the extension wiring functions as a different potential field.

[Another Example of Power Transfer-Side Compensation Circuit and Power Reception-Side Compensation Circuit]

Furthermore, in the above-described configuration, the coil L2 included in the power reception-side compensation circuit 22 may be disposed on the power transfer-side compensation circuit 12 side.

Figure 2B:
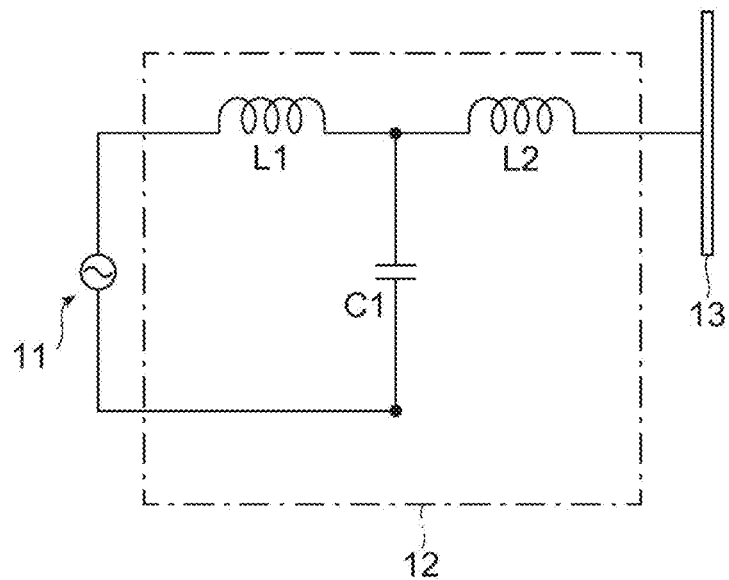

That is, as illustrated in FIG. 2B, the power transfer-side compensation circuit 12 according to another example of the present embodiment includes the coil L1, the capacitor C1, and the coil L2. Here, one end of the coil L1 is connected to one end of the output terminal of the AC power source unit 11. Furthermore, the other end of the coil L1 is connected to one end of the capacitor C1, and is connected to one end of the coil L2. Furthermore, the other end side of the coil L2 is connected to the power transfer plate 13. Note that the other end of the capacitor C1 is connected to the other end of the output terminal of the AC power source unit 11.

Figure 3B:
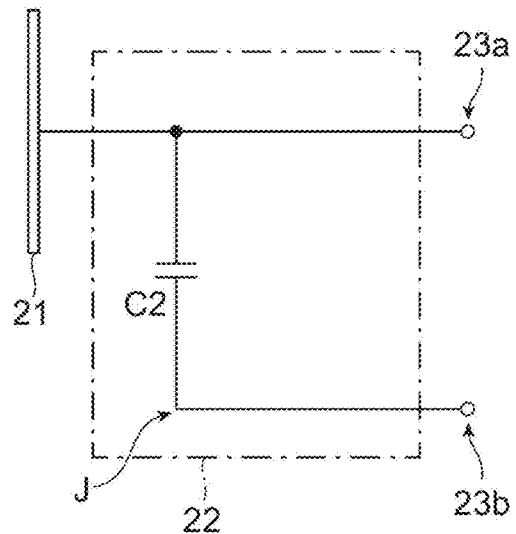

Furthermore, as illustrated in FIG. 3B, the power reception-side compensation circuit 22 of this example includes the capacitor C2. One end of the capacitor C2 is connected to the power reception plate 21 and connected to the first terminal 23a. Furthermore, the other end of the capacitor C2 is connected to the second terminal 23b of the output circuit 23.

The power reception device 20 including the power reception-side compensation circuit 22 of this example can be reduced in size. The reducing in size is suitable, for example, in a case where the power reception device 20 is configured as a device for supplying power to devices such as a pacemaker embedded in the human body, a nerve stimulation device, and various signal detection devices.

[Configuration Example of Output Circuit]

Figure 5:
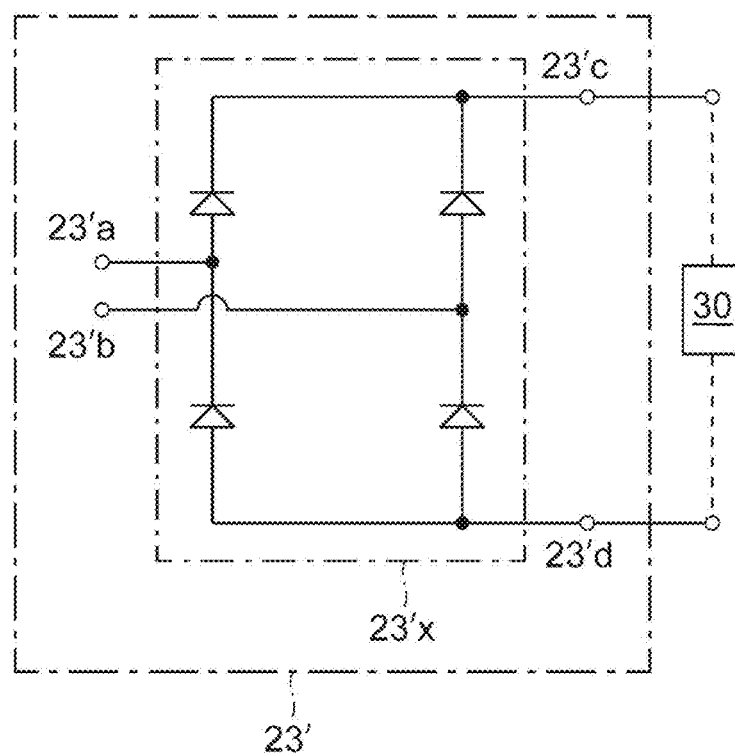
FIG. 5 is a schematic circuit diagram illustrating another example of an output circuit of a power reception device according to the embodiment of the present invention.

Furthermore, instead of the output circuit 23 of the present embodiment, an output circuit 23' including a rectifier circuit unit 23'x may be used. As illustrated in FIG. 5, the output circuit 23' includes the rectifier circuit unit 23'x including a diode bridge D. The rectifier circuit unit 23'x converts an alternating current input from a first terminal 23'a corresponding to the first terminal 23a of the output circuit 23 and a second terminal 23'b corresponding to the second terminal 23b of the output circuit 23 into a direct current, and outputs the direct current to a first output terminal 23'c (positive electrode) and a second output terminal 23'd (negative electrode). Note that since a configuration and an operation of the diode bridge D are widely known, a detailed description thereof will be omitted here.

In this example, the load 30 is connected between the first output terminal 23'c (positive electrode) of the output circuit 23' and the second output terminal 23'd (negative electrode) of the output circuit 23'.

Note that, here, an example of a circuit that performs full-wave rectification is used as the rectifier circuit unit 23'x, but a circuit that performs half-wave rectification may be used as the rectifier circuit unit 23'x instead of the circuit that performs full-wave rectification according to the use.

[Impedance Matching]

Furthermore, in the present embodiment, the reactance and capacitance of the coils L1 and L2 and the capacitors C1 and C2 in the power transfer-side compensation circuit 12 and the power reception-side compensation circuit 22 are determined as below.

That is, in the present embodiment, constants of circuit elements included in the power transfer-side compensation circuit 12 and the power reception-side compensation circuit 22 are determined such that impedances of a power transfer-side circuit and a power reception-side circuit, which are coupled via coupling capacitance Cc formed by capacitive coupling between the power transfer plate 13 and the power reception plate 21 match each other. Specifically, when a result is used, the result obtained by analyzing a case where the power transfer-side compensation circuit 12 and the power reception-side compensation circuit 22, which are illustrated in FIG. 2(a) and FIG. 3A, are used, by a method of analyzing a node voltage with each of the capacitors (including coupling capacitance Cc) C1, C2, and Cc, the coils L1 and L2, and a load Z as a resistor, the reactance of the coil L1 is represented by Equation below.

[Mathematical formula 1]

$$L_1 = \frac{\left(1 + \frac{R_x}{R_C}\right)}{\omega^2 C_1 \left(1 + \frac{R_x}{R_C}\right) + \omega^2 C_C} \quad (1)$$

where RC indicates impedance of coupling capacitance Cc with respect to an alternating current of an angular frequency $\omega = 2\pi f$ (f is a frequency), Rx indicates combined impedance of the power reception-side compensation circuit 22 and load Z with respect to an alternating current of an angular frequency $\omega$, and in a case of the circuit illustrated in FIG. 3A (impedance of the load Z is RL and an imaginary unit is j), Rx is represented by Equation below.

$$R_x = \frac{\frac{1}{j\omega C_2}(j\omega L_2 + R_L)}{\frac{1}{j\omega C_2} + j\omega L_2 + R_L}$$

Furthermore, the reactance of the coil L2 is determined using the reactance of the coil L1, the capacitance C1 of the capacitor C1, and the capacitance Cc of the coupling capacitance so as to satisfy the following condition.

[Mathematical formula 2]

$$L_2 \geq \frac{C_C}{\omega(C_C - C_2)}\left(\frac{R_L C_2}{C_C} + \frac{1}{\omega C_C} - R_L\right) \quad (2)$$

Furthermore, Equation (1) is solved for f, and the resonance frequency f is represented by Equation as below.

[Mathematical formula 3]

$$f = \frac{1}{2\pi}\sqrt{\frac{\left(1 + \frac{R_x}{R_C}\right)}{\left(1 + \frac{R_x}{R_C}\right)L_1 C_1 + L_1 C_C}} \quad (3)$$

Therefore, when the capacitance Cc of the coupling capacitance is determined in consideration of a relative dielectric constant of air or a dielectric sandwiched between the power transfer plate 13 and the power reception plate 21, the power transfer efficiency can be improved by adjusting the distance and alignment between the power transfer plate 13 and the power reception plate 21 (to what extent the power reception plate 21 is included in the overlap region) or controlling the angular frequency co of the alternating current output by the AC power source unit 11 to perform adjustment so as to satisfy the Equations (1) to (3).

[Example of Load]

Moreover, in the example of the present embodiment, the load 30 connected to the power reception device 20 is, for example, a medical device such as a pacemaker embedded in a body such as a human body, a nerve stimulation device, or various signal detection devices. The load 30 may include a secondary battery, a microcomputer, a microprocessor, a memory, a wireless communication module, a digital signal processor, an RF detector, a filter, and the like.

Furthermore, when power is supplied from the power reception device 20, the load 30 may output a signal indicating that the power is supplied (or a signal indicating the magnitude of the supplied power) via a wireless communication module or the like.

[Implementation Example of Pacemaker]

The power transfer system 1 of the present embodiment is useful in a situation in which it is difficult to supply power by wire. For example, the power transfer system 1 of the present embodiment is suitably applied to a device that generates stimulation to nerves or the like, which is embedded in the human body, and which is used for spinal cord stimulation therapy, sacral nerve stimulation therapy, vagal nerve stimulation therapy, deep brain stimulation therapy, and the like, a cardiac pacemaker, a signal detection device that detects an electrical signal at various sites in the human body, and the like. In these examples, the power reception device 20 is disposed to be embedded in a body such as a human body (note that, here, the human body is taken as an example, but the power reception device 20 may be embedded in the body of an animal other than a human). Furthermore, the power transfer device 10 is disposed outside the body such as the human body and used.

Figure 6A:
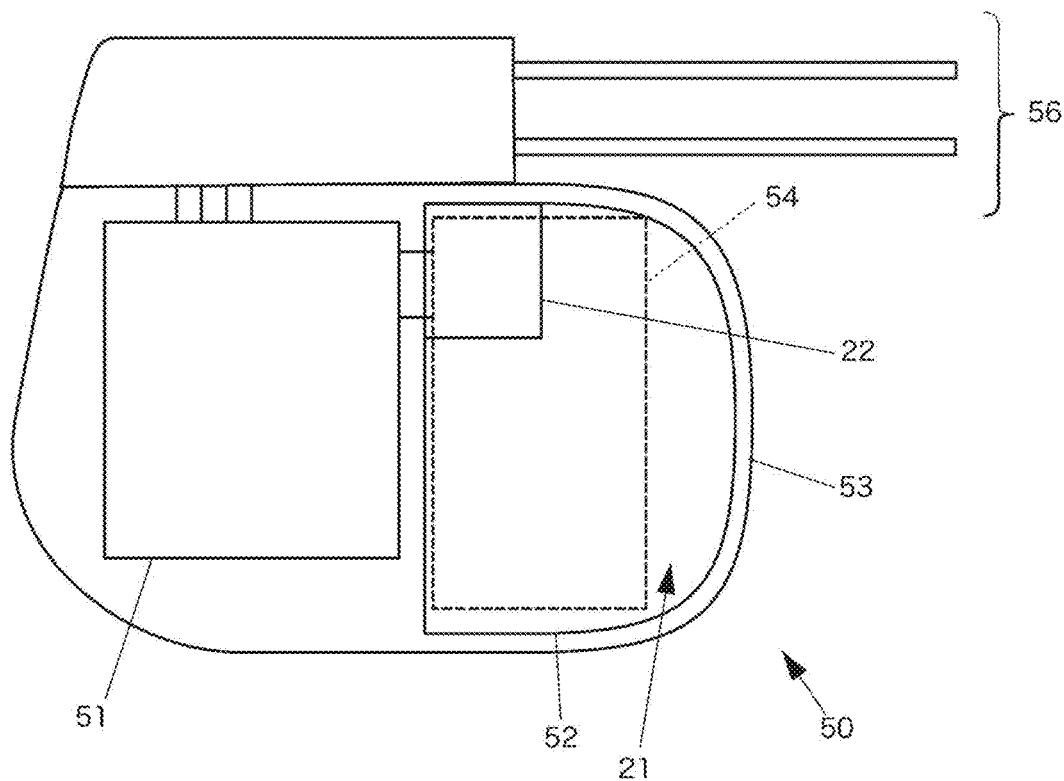
FIGS. 6A and 6B are schematic explanatory diagrams illustrating an implementation example of a power transfer system according to the embodiment of the present invention.

As an example, FIG. 6 illustrates a schematic example in which the power transfer system 1 of the present embodiment is applied to a cardiac pacemaker. As illustrated in FIG. 6A, in this example, a cardiac pacemaker 50 includes a generator circuit unit 51 and a power supply unit 52, which are contained in a thin casing 53.

Figure 6B:
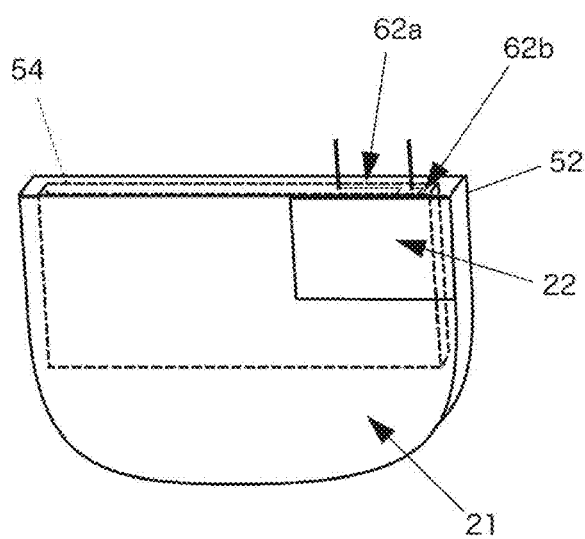

The power supply unit 52 includes a secondary battery 54 including two terminals of a positive electrode and a negative electrode. Furthermore, in this example of the present embodiment, a surface of the power supply unit 52 on one surface side of the casing 53 is formed by a conductor, a surface formed by the conductor is the power reception plate 21, and the power reception-side compensation circuit 22 is disposed on a front surface (surface facing the outside of the casing 53) or a back surface of the power reception plate 21. The power reception-side compensation circuit 22 of this example may be based on any of the examples of FIGS. 3(*a*) and 3(*b*). The secondary battery 54 is connected as a load of the power reception-side compensation circuit 22 via the wirings 62*a* and 62*b*. In this example of the present embodiment, the negative electrode of the secondary battery 54 is connected to the common potential point (GND) together with the wiring 62*b* (FIG. 6B).

Furthermore, the secondary battery 54 also supplies power to the generator circuit unit 51. The generator circuit unit 51 is similar to that of a general cardiac pacemaker, and a pacing lead 56 is led out from the generator circuit unit 51. Here, the wiring on the negative electrode side of the generator circuit unit 51, that is, on the negative electrode side of the pacing lead 56 is also connected to the common potential point (GND) together with the negative electrode of the secondary battery 54 and the wiring 62*b*.

The pacing lead 56 is led out from a part of the casing 53 and is attached to the heart via a pacing electrode (not illustrated) disposed at a distal end of the pacing lead 56.

The cardiac pacemaker of this example is embedded in the human body with the normal direction of the power reception plate 21 set in a front-back direction of the human body.

One of problems in the case of applying the power transfer system to the cardiac pacemaker is that it is necessary to dispose a power reception device that receives power wirelessly in the casing 53. That is, in this example, since it is difficult to dispose the power reception-side compensation circuit 22 at a place away from the power reception plate 21, the power reception-side compensation circuit 22 is disposed on the back surface of the power reception plate 21. However, in this case, it becomes difficult to separate the other end (wiring J in FIG. 3, that is, the wiring 22C in FIG. 4) of the capacitor C2 of the power reception-side compensation circuit 22 from one end (side connected to the power reception plate 21) of the capacitor C2.

Therefore, in this example, as described above, the negative electrode of the power reception-side compensation circuit 22, that is, the wiring 62*b* is connected to the common potential point together with the negative electrode of the pacing lead 56 and the negative electrode of the secondary battery 54, and thus the wiring on the negative electrode side of the power reception-side compensation circuit 22 (wiring having a potential equal to that of the wiring J in FIG. 3) is extended to a position (heart in this example) separated from one end (side connected to the power reception plate 21) of the capacitor C2.

In this example of the present embodiment, when power transfer is started by bringing the power transfer plate 13 of the power transfer device 10 into contact with the surface of the human body on a side closer to the power reception plate 21, in the power reception-side compensation circuit 22 that receives power from the power transfer device 10, an end point of the pacing lead 56 on the heart side, which has the same potential as that of the wiring 62*b*, functions as a different potential field (that is, the pacing lead 56 functions as an extension wiring), and as a result, a potential difference is generated between both end points of the capacitor C2. Therefore, power is supplied to the secondary battery 54 as a load, and the secondary battery 54 is charged.

[Another Example of Power Transfer Element and of Power Reception Element]

In the above description, the power transfer element is a plate-shaped element (power transfer plate 13), and the power reception element is similarly a plate-shaped element (power reception plate 21), but the present embodiment is not limited to this.

In another example of the present embodiment, the power transfer element may be an element obtained by molding a conductor into a first predetermined shape, and the power reception element may be an element obtained by molding a conductor into a second predetermined shape. As an example, the first predetermined shape is a coil shape in which one end side is connected to the AC power source unit 11 and the other end is open. In this case, the second predetermined shape of the corresponding power reception element is a coil shape in which one end is connected to the power reception-side compensation circuit 22 and the other end is open or connected to a location other than one end of the power reception-side compensation circuit 22.

Figure 10:
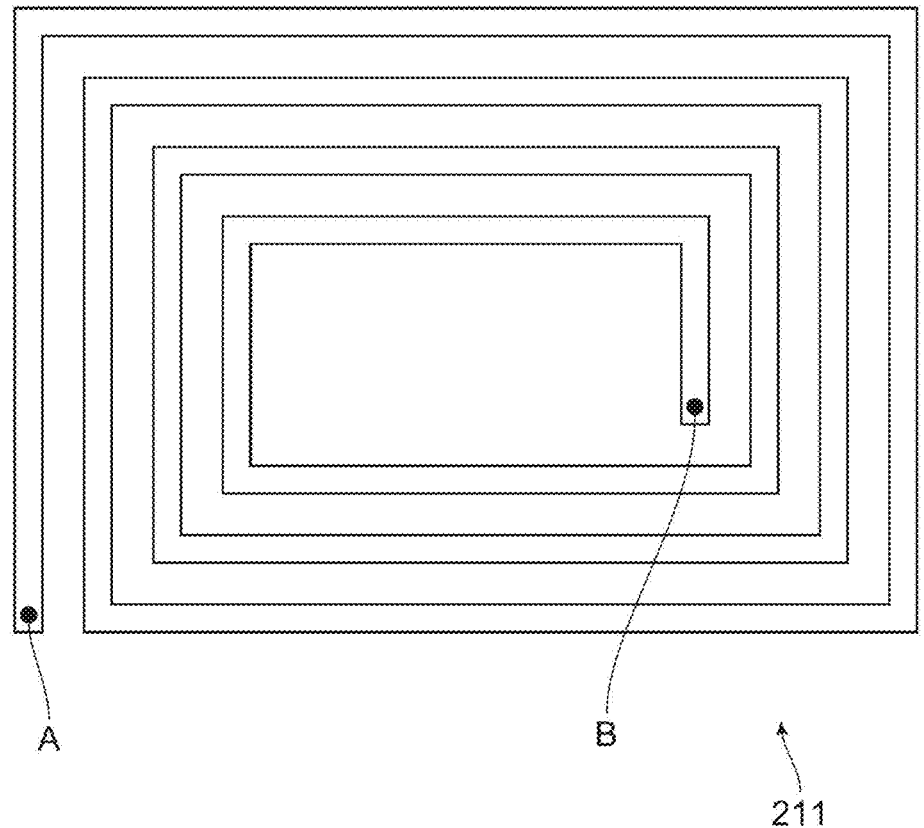
FIG. 10 is an explanatory diagram illustrating an example showing a shape of a power transfer element and a shape of a power reception element in a power transfer system according to the embodiment of the present invention.
Figure 11:
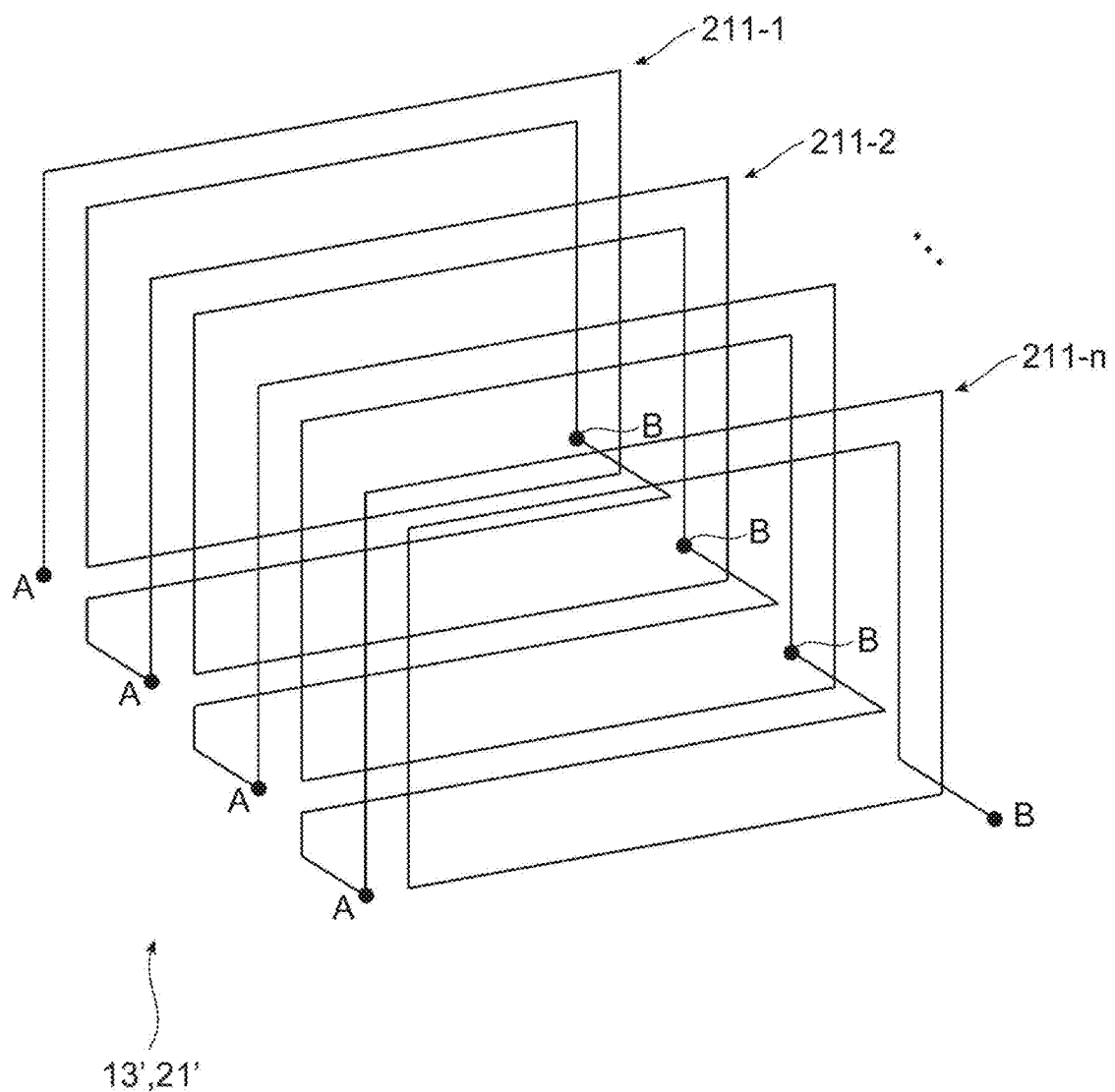
FIG. 11 is another explanatory diagram illustrating an example showing a shape of a power transfer element and a shape of a power reception element in a power transfer system according to the embodiment of the present invention.

Specifically, as illustrated in FIGS. 10 and 11, each of coils 13' and 21' having the first and second predetermined shapes is formed by stacking winding wires 211-1, 211-2, . . . , and 211-*n*, which are disposed by winding a conductive wire in a rectangular spiral shape in a plane (in each layer of a multilayer substrate) in multiple layers (n layers in this case). Note that the number of windings of the winding wire in FIG. 10 is an example, and the number of times of winding may be greater or smaller than the number of windings of the winding wire in FIG. 10. Furthermore, the arrangement of the winding wires is not uniform, and there may be a region in which the winding wires are closely disposed and a region in which the winding wires are disposed sparsely. Furthermore, in FIG. 11, in order to make the illustrated content easy to understand, the number of times of winding is relatively reduced, and is illustrated as a perspective view.

Here, as illustrated in FIG. 10, a winding wire 211-$i$ ($i$=1, 2 . . . , n) formed in the i-th layer is wound from the outside to the inside with an end point Ai at the lower left corner of the spiral shape as a starting point, and an end point Bi of the conductive wire close to the center is electrically connected to an end point Ai+1 of a winding wire 211-($i$+1) of the adjacent next layer or an end point Bn of the last layer (which is a layer closest to the power reception element in the power transfer element and a layer farthest from the power transfer element in the power reception element, hereinafter, referred to as a final layer) is a terminal. The terminal of the end point Bn is an open end in one example of the present embodiment, and is connected to another circuit in another example.

As described above, in the example of the present embodiment in which the coils 13' and 21' are used as the power transfer element and the power reception element, it is preferable that the power transfer-side compensation circuit 12 and the power reception-side compensation circuit 22 are as follows instead of those in the examples illustrated in FIGS. 2 and 3.

That is, regarding an example of the power transfer-side compensation circuit 12 in this example, FIGS. 12($a$) and 12($b$) respectively illustrates an example of a case where the power transfer-side compensation circuit 12 is connected to one end of a coil-shaped power transfer element formed by winding a conductive wire and an example of a case where the power transfer-side compensation circuit 12 is connected to both ends of the coil-shaped power transfer element.

Figure 12A:
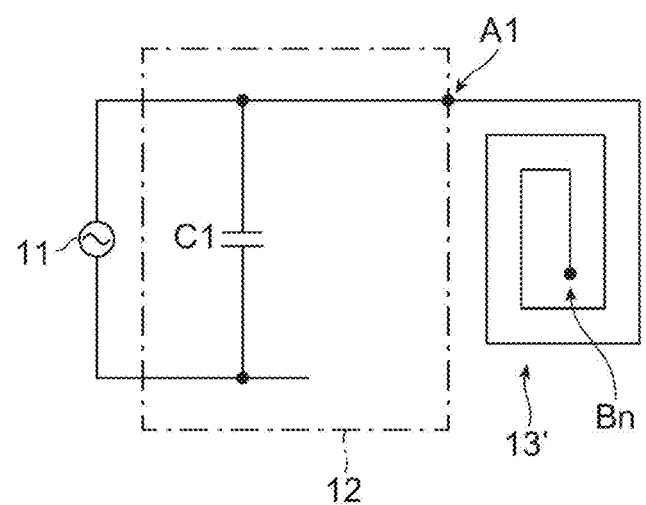
FIGS. 12A and 12B are schematic circuit diagrams illustrating an example of a power transfer-side compensation circuit in a power transfer system according to the embodiment of the present invention.

As illustrated in FIG. 12A, in a case where one end of a coil-shaped power transfer element is connected to the power transfer-side compensation circuit 12, the power transfer-side compensation circuit 12 includes the capacitor C1. One end of the capacitor C1 is connected to one terminal of the AC power source unit 11, and the other end of the capacitor C1 is connected to the other terminal of the AC power source unit 11. Furthermore, one end of the capacitor C1 is connected to one end of the coil 13' which is the power transfer element (point A1 of the winding wire 211-1 of the first layer (layer farthest from the power reception element) of the coil 13'). In this example, the other end of the coil 13' (point Bn (terminal Bn) of the winding wire 211-$n$ of the final layer) is an open end.

Figure 12B:
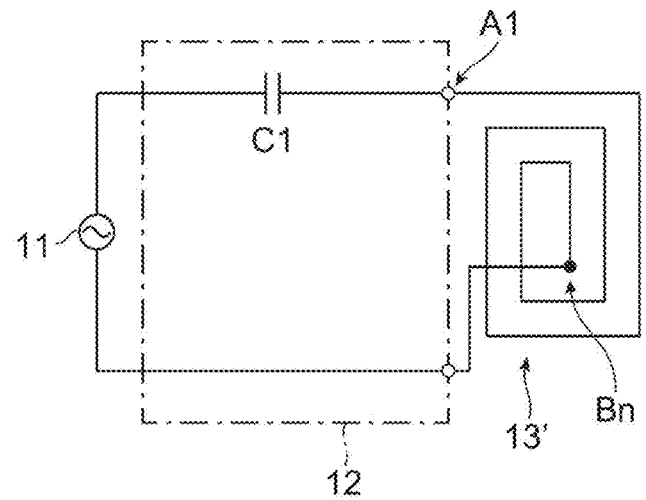

Furthermore, also in a case where both ends of the coil 13' as the power transfer element are connected to the power transfer-side compensation circuit 12, the power transfer-side compensation circuit 12 includes the capacitor C1 as illustrated in FIG. 12B, but a connection mode is different.

In this example in which both ends of the coil 13' as the power transfer element are connected, one end of the capacitor C1 of the power transfer-side compensation circuit 12 is connected to one terminal of the AC power source unit 11, and the other end of the capacitor C1 is connected to one end of the coil 13' as the power transfer element (point A1 of the winding wire 211-1 of the first layer (layer on a side farthest from the power reception element) of the coil 13').

Furthermore, the other end of the coil 13' (point Bn (terminal Bn) of the winding wire 211-$n$ of the final layer) is connected to the other terminal of the AC power source unit 11 via the power transfer-side compensation circuit 12 (or not via the power transfer-side compensation circuit 12).

Figure 13A:
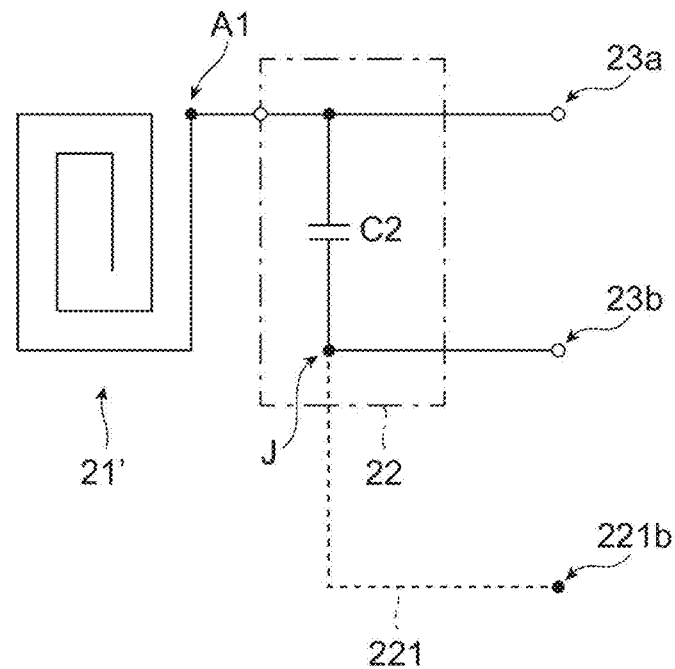
FIGS. 13A and 13B are schematic circuit diagrams illustrating an example of a power reception-side compensation circuit in a power transfer system according to the embodiment of the present invention.
Figure 13B:
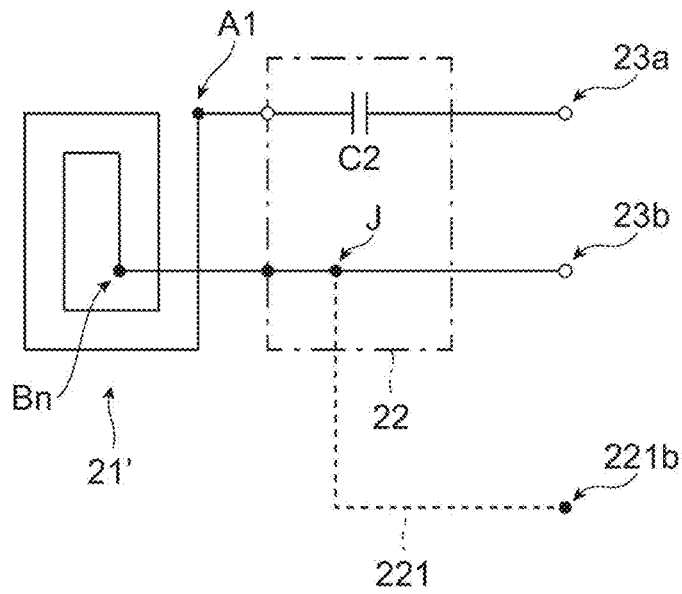

Furthermore, the power reception-side compensation circuit 22 is as illustrated in FIGS. 13($a$) and 13($b$). FIG. 13A illustrates an example of connection to one end of a coil-shaped power reception element formed by winding a conductive wire. Furthermore, FIG. 13B illustrates an example of connection to both ends of a coil-shaped power reception element formed by winding a conductive wire.

In a case where one end of a coil-shaped power reception element is connected to the power reception-side compensation circuit 22, the power reception-side compensation circuit 22 includes the capacitor C2 as illustrated in FIG. 13A One end of the capacitor C2 is connected to one end of the coil 21' which is the power reception element (point A1 of the winding wire 211-1 of the first layer (layer closest to the power transfer element) of the coil 21') and connected to the first terminal 23$a$ of the output circuit 23. Furthermore, the other end of the capacitor C2 is connected to a second terminal 23$b$ of the output circuit 23.

In this example, the other end of the coil 21' (point Bn (terminal Bn) of the winding wire 211-$n$ of the final layer) is an open end.

Furthermore, also in a case where both ends of the coil 21' as the power reception element are connected to the power reception-side compensation circuit 22, the power reception-side compensation circuit 22 includes the capacitor C2 as illustrated in FIG. 13B, but a connection mode is different.

In this example in which both ends of the coil 21' as the power reception element are connected, one end of the capacitor C2 of the power reception-side compensation circuit 22 is connected to one end of the coil 21' (point A1 of the winding wire 211-1 of the first layer (layer on a side closest to the power transfer element) of the coil 21'), and the other end of the capacitor C2 is connected to the first terminal 23$a$ of the output circuit 23.

Furthermore, the other end of the coil 21' (point Bn (terminal Bn) of the winding wire 211-$n$ of the final layer) is connected to the second terminal 23$b$ of the output circuit 23.

In these examples of the present embodiment, the power transfer element or the power reception element has the above-described coil shape. Furthermore, in this example, a magnetic flux formed by the coil 13' of the power transfer element is caused to pass through the coil 21' of the power reception element. That is, here, the coils 13' and 21' are disposed such that normal directions of the layers of the coils 13' and 21' coincide with each other. Furthermore, at least a part of the conductive wire forming the coil 21' as the power reception element is included in the columnar movement trajectory (overlap region) formed by virtually moving the rectangle circumscribing the winding wire 211-$i$ of each layer of the coil 13' of the power transfer element in the normal direction.

In this example, the coil 13' as the power transfer element and the coil 21' as the power reception element are electrically and magnetically coupled (capacitively coupled and inductively coupled) to each other when AC power of a predetermined frequency is supplied from the AC power source unit 11. Here, the frequency of the AC power supplied by the AC power source unit 11 is determined to be a frequency at which the coil as the power transfer element and the coil as the power reception element are electrically and magnetically coupled by capacitive coupling and inductive coupling when the coil as the power transfer element and the coil as the power reception element are disposed to face each other in a range of a predetermined distance by performing an experiment in advance.

In this example, the centers of the coil 13' as the power transfer element and the coil 21' as the power reception element may not necessarily have to coincide with each other in a plan view, as will be described later, as long as there is a portion overlapping with each other (that is, as long as at least a part of the conductive wire of the coil 21' as the power reception element is included in the overlap region), the alignment between the centers may have a certain degree of deviation. Furthermore, the power transfer element and the power reception element may not necessarily be disposed strictly in parallel as long as the power transfer element and the power reception element can be capacitively or inductively coupled to each other.

In a case where the AC power at the frequency of the capacitive coupling or the inductive coupling is supplied, the electric field formed by the coil 13' as the power transfer element has a direction substantially perpendicular to a surface of the layer of the coil 13' also in this example of the present embodiment. Therefore, the potential field formed based on the electric field is parallel to the surface of the layer of the coil 13' as the power transfer element at least in the vicinity of the power transfer element, and the magnitudes of the potentials on the potential fields at positions different from each other from the coil 13' as the power transfer element varies with time, but the potential field decreases with distance from the coil 13' as the power transfer element.

Here, the other end side 22C of the capacitor C2 of the power reception-side compensation circuit 22 is disposed such that a distance from the coil 13' as the power transfer element to the other end side 22C of the capacitor C2 of the power reception-side compensation circuit 22 is greater than a distance from the coil 13' as the power transfer element to the coil 21' as the power reception element. Furthermore, the other end side 22C of the capacitor C2 may be disposed such that at least a part of the other end side 22C of the capacitor C2 is included in the overlap region of the coil 13' as the power transfer element. Accordingly, the other end side 22C of the capacitor C2 functions as a different potential field, a difference is generated between the potential of the terminal (terminal connected to one end of the capacitor C2 of the power reception-side compensation circuit 22) of the coil 21' of the power reception element and the potential of the other end side 22C of the capacitor C2 of the power reception-side compensation circuit 22, and a current flows through the load connected between potentials.

Here, a relationship between the distance Dr between the other end of the capacitor C2 and the power transfer element and the distance Dp between the power transfer element and the power reception element may be similar to that in the example described above. In this case, the entire power reception-side compensation circuit 22 functions as a different potential field.

Moreover, the extension wiring is connected to the other end (wiring J in FIG. 3, that is, the wiring 22C in FIG. 4) of the capacitor C2 of the power reception-side compensation circuit 22, and the end of the extension wiring may be disposed at a position greater than the distance Dp by a predetermined distance d or more. Furthermore, this position may be outside the overlap region of the power transfer element, or may be within the overlap region of the power transfer element. Note that the end of the extension wiring may be an open end, or may be connected to another conductor, GND, another circuit configuration, or the like as long as it is not short-circuited to one end of the capacitor C2. In this example, the end of the extension wiring functions as a different potential field.

Furthermore, an extension wiring 221 may be connected to the other end (wiring J in FIG. 13A) of the capacitor C2 of the power reception-side compensation circuit 22 also in the example illustrated in FIG. 13A of the present embodiment, and the wiring J of the power reception-side compensation circuit 22 connected to the terminal 23b of the output circuit 23 in the example illustrated in FIG. 13B, and an end 221b of the extension wiring 221 may be disposed at a position greater than the distance Dp between the coil 13' as the power transfer element and the coil 21' as the power reception element by a predetermined distance d or more. Furthermore, the position of the end 221b may be outside the overlap region of the coil 13' as the power transfer element, or may be within the overlap region of the coil 13' as the power transfer element. Note that the end of the wiring may be an open end, or may be connected to another conductor, GND, another circuit configuration, or the like as long as it is not short-circuited to the wiring J. In this example, the end of the extension wiring functions as a different potential field.

[Transmission and Reception of Data]

Moreover, in the above description, the power transfer element and the power reception element are used for power transfer, but the example of the present embodiment is not limited to this, and the power transfer element and the power reception element may be used for data transmission. In this case, the data can be transmitted bidirectionally (from the power transfer element to the power reception element, or from the power reception element to the power transfer element). In the example used for data transmission, both the power transfer element and the power reception element are referred to as a transmission and reception element.

In this example of the present embodiment, the transmission and reception element may be, for example, similar to the coil-shaped power transfer element or coil-shaped power reception element illustrated in FIG. 11.

As described above, the power transfer system 1 of the present embodiment is useful in a situation in which it is difficult to supply power by wire. For example, the present invention can be used for a stimulation generation device that is embedded in a human body and is used in a spinal cord stimulation therapy, a deep brain stimulation therapy, and the like.

In such an example, the load 30 may include a secondary battery, a microcomputer, a microprocessor, a memory, a wireless communication module, a digital signal processor, an RF detector, a filter, a stimulation generator, a stimulation electrode, various sensors, and the like.

Figure 14:
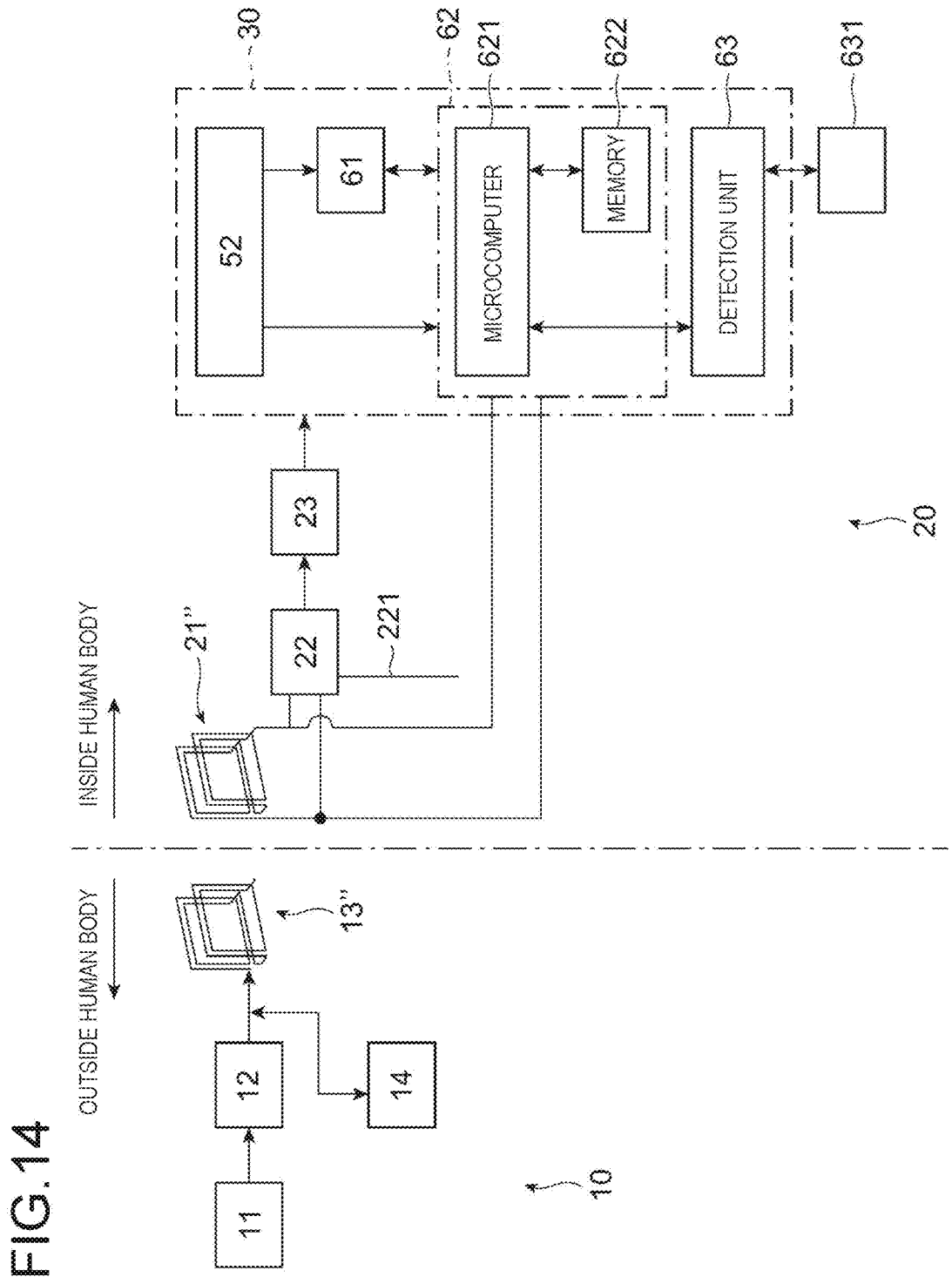
FIG. 14 is a block diagram illustrating a schematic configuration of a power transfer system according to the embodiment of the present invention.

For example, FIG. 14 illustrates a schematic example in which the power transfer system 1 of the present embodiment is applied to a device used inside the human body. As illustrated in FIG. 14, in the power transfer system 1 of this example, the power transfer device 10 is disposed outside the human body. Furthermore, the power reception device 20 is embedded inside the human body. Note that, here, the human body is taken as an example, but the power reception device 20 may be embedded in the body of an animal other than a human.

The power transfer device 10 includes the AC power source unit 11, the power transfer-side compensation circuit 12, a single transmission and reception element 13", and an information processing unit 14 (corresponding to a first information processing unit of the present invention). Furthermore, the power reception device 20 includes a single transmission and reception element 21", the power reception-side compensation circuit 22, and the output circuit 23, and includes, as the load 30, the power supply unit 52, a stimulation circuit unit 61, an information processing unit 62 (corresponding to a second information processing unit of the present invention), and a detection unit 63. Note that components having the same configurations as those described above are denoted by the same reference numerals, and a repeated description will be omitted.

The transmission and reception element 13" and 21" are configured by stacking the coil illustrated in FIG. 10 in multiple layers.

Furthermore, the information processing unit 14 includes a program control device such as a processor. As will be described below, the information processing unit 14 transmits and receives information to and from the power reception device 20, and executes preset processing.

Figure 15A:
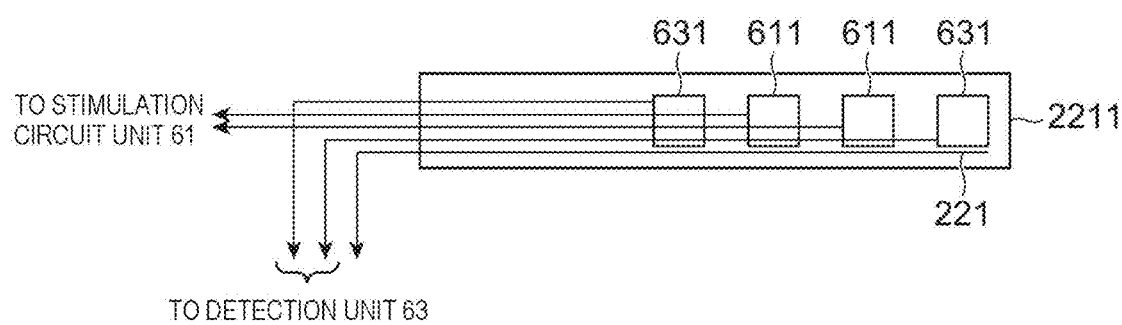
FIGS. 15A and 15B are explanatory diagrams illustrating an example of an end configuration of an extension wiring serving as a different potential field in a power transfer system according to the embodiment of the present invention.

In accordance with an instruction input from the information processing unit 62, the stimulation circuit unit 61 applies electrical stimulation to a predetermined first site in the human body between a pair of stimulation electrodes 611 via a pair of the stimulation electrodes 611 disposed at a predetermined interval (for example, an interval of 2 mm or more). Such a stimulation circuit unit 61 is widely known, for example, for use in the spinal cord stimulation therapy, and thus a detailed description thereof will be omitted here. Here, as illustrated in FIG. 15A, the stimulation electrodes 611 may be disposed on a element (extension wiring element 2211) on which the extension wiring 221 is disposed. That is, in the present embodiment, the extension wiring 221 is disposed on, for example, a thin-film flexible substrate as the extension wiring element 2211 or a substrate formed in an annular shape, and a pair of the stimulation electrodes 611 are disposed on end points of the wirings extended from the stimulation circuit unit 61 and disposed on the extension wiring element 2211.

The information processing unit 62 includes a microcomputer. As will be described later, the information processing unit 62 transmits and receives information to and from the power transfer device 10. Furthermore, the information processing unit 62 executes preset processing and outputs an instruction to the stimulation circuit unit 61. Moreover, the information processing unit 62 includes a microcomputer 621 and a memory 622. The operation of the microcomputer 621 will be described later.

The detection unit 63 is connected to a sensor 631, measures various electrical states generated at a second predetermined site of the human body in which the sensor 631 is disposed, and outputs the measured states to the information processing unit 62. Here, the second predetermined site is, for example, a site of a membrane, a nerve, or other tissues, and the sensor 631 measures a signal as a membrane potential, a nerve action potential, an organ pressure, a tissue impedance, a temperature, or other biomarkers, and outputs the signal to the information processing unit 62.

In an example of the present embodiment, as illustrated in FIG. 15A, a pair of electrodes functioning as the sensor 631 of the detection unit 63 may also be disposed on the extension wiring element 2211. Furthermore, a pair of the electrodes of the sensor 631 are also disposed at a predetermined interval (for example, 2 mm or more), and are electrically connected to the detection unit 63 via wirings formed on the extension wiring element 2211.

Note that a total of four electrodes including two electrodes functioning as the stimulation electrode 611 and two electrodes functioning as the sensor 631 are insulated from each other. However, in a case where one of the stimulation electrodes 611 and one of the electrodes of the sensor 631 both have a common potential, the electrodes as the common potential may be short-circuited.

Here, an operation example of the microcomputer 621 of the information processing unit 62 will be described. When receiving the signal input from the detection unit 63, the microcomputer 621 stores information indicating the content of the signal in the memory 622. The microcomputer 621 transmits the information stored in memory 622 to the power transfer device 10 at a predetermined timing. Furthermore, the information processing unit 62 may control the frequency and intensity of an electrical signal for stimulation generated by the stimulation circuit unit 61 on the basis of the signal measured by the detection unit 63, the pulse width in a case where the electrical signal is a pulse signal, and further, a timing and time of giving the stimulation.

In these examples of the present embodiment, the information processing unit 14 is connected to the transmission and reception element 13" of the power transfer device 10 and transmits and receives information via the transmission and reception element 13". For transmission and reception of this information, various widely known transmission and reception formats such as NFC, Wi-Fi, Bluetooth (registered trademark), RFID wireless communication standards, or the like can be adopted. Furthermore, in the present embodiment, the information processing unit 14 may transmit and receive this information when power is not being transferred.

Similarly, the information processing unit 62 is connected to the transmission and reception element 21" of the power reception device 20, and transmits and receives information via the transmission and reception element 21". The information processing unit 62 transmits and receives information in the same transmission and reception format as the transmission and reception format for information, which is used by the information processing unit 14 of the power transfer device 10. The information processing unit 62 may also transmit and receive the information when power is not being transferred.

Furthermore, here, the information processing unit 62 controls the frequency and the like of the electrical signal for stimulation generated by the stimulation circuit unit 61 on the basis of the signal output by the detection unit 63 and measured by the sensor 631, but the present embodiment is not limited to this. For example, the information processing unit 62 may transmit information indicating the signal measured by the detection unit 63 to the information processing unit 14 of the power transfer device 10 via the transmission and reception element 21" and 13".

In this example, the information processing unit 14 receives the information transmitted by the information processing unit 62, and determines parameters such as the frequency and intensity of an electrical signal for stimulation generated by the stimulation circuit unit 61 on the basis of the signal indicated by the information, the pulse width in a case where the electrical signal is a pulse signal, and further, a timing and time of giving the stimulation. The information processing unit 14 transmits information regarding the determined parameter to the information processing unit 62 via the transmission and reception element 13" and 21".

On the basis of the parameter indicated by the information transmitted from the information processing unit 14, the information processing unit 62 controls the stimulation circuit unit 61 so as to apply an electrical stimulation determined by the parameter to the first predetermined site at a timing determined by the parameter.

Furthermore, in this example, the information processing unit 14 may present the information transmitted from the information processing unit 62 or the like of the power reception device 20 to a user, and determine the parameter and the like according to an instruction of the user. Furthermore, the information processing unit 14 may transmit the information transmitted from the information processing unit 62 or the like of the power reception device 20 to a predetermined server apparatus via a network, receive the parameter determined by calculation in the server apparatus, and transmit the received parameter as it is to the power reception device 20.

[Example without Battery]

Furthermore, the power reception device 20 of the present embodiment may not necessarily include a rechargeable battery. In this example, when the power reception device 20 is operated, the power transfer device 10 is disposed at a place at which power can be supplied to the power reception device 20. Furthermore, in such an example, the power reception device 20 may include an element such as a capacitor, which can store the supplied power to cope with a temporary power supply failure or a temporary increase in power consumption and supply the power when the power is insufficient. Since a widely known method can be adopted for the arrangement of the capacitor, a detailed description thereof will be omitted here.

[Operation Example of Information Processing Unit]

Next, an example of applying stimulation by the operations of the information processing units 14 and 62 will be described. In the following example of the present embodiment, the power reception device 20 is disposed inside the human body, and the power transfer device 10 is disposed outside the human body. For example, the power transfer device may be fixed to an outer surface of the human body (position at which power and information can be transmitted and received via the transmission and reception element 13" and 21") corresponding to the position at which the power reception device 20 is embedded with a belt or the like. As described above, in a case where the power transfer device 10 is disposed at a position at which power can be supplied during the operation of the power reception device 20, the power reception device 20 does not need to include a battery as described above.

Furthermore, here, the information processing unit 62 controls each unit according to an instruction (including information specifying an applying mode of a stimulation) received from the information processing unit 14.

As illustrated in FIG. 16, the power reception device 20 receives power from the power transfer device 10 and is turned on from a state in which the power source is turned off (S1). At this time, the information processing unit 62 of the power reception device 20 determines whether or not sufficient power is supplied (S2), and when the sufficient power is not supplied (Step S2: No), the information processing unit 62 may notify the power transfer device 10 of the fact. When receiving this notification, the information processing unit 14 of the power transfer device 10 notifies the user of the power transfer device 10 that the power supply to the power reception device is not sufficient (S3).

On the other hand, in Step S2, when the information processing unit 62 determines that the sufficient power is supplied (S2: Yes), the processing of controlling each unit is started according to an instruction (including the information for specifying the stimulation application mode) received from the information processing unit 14.

Figure 17:
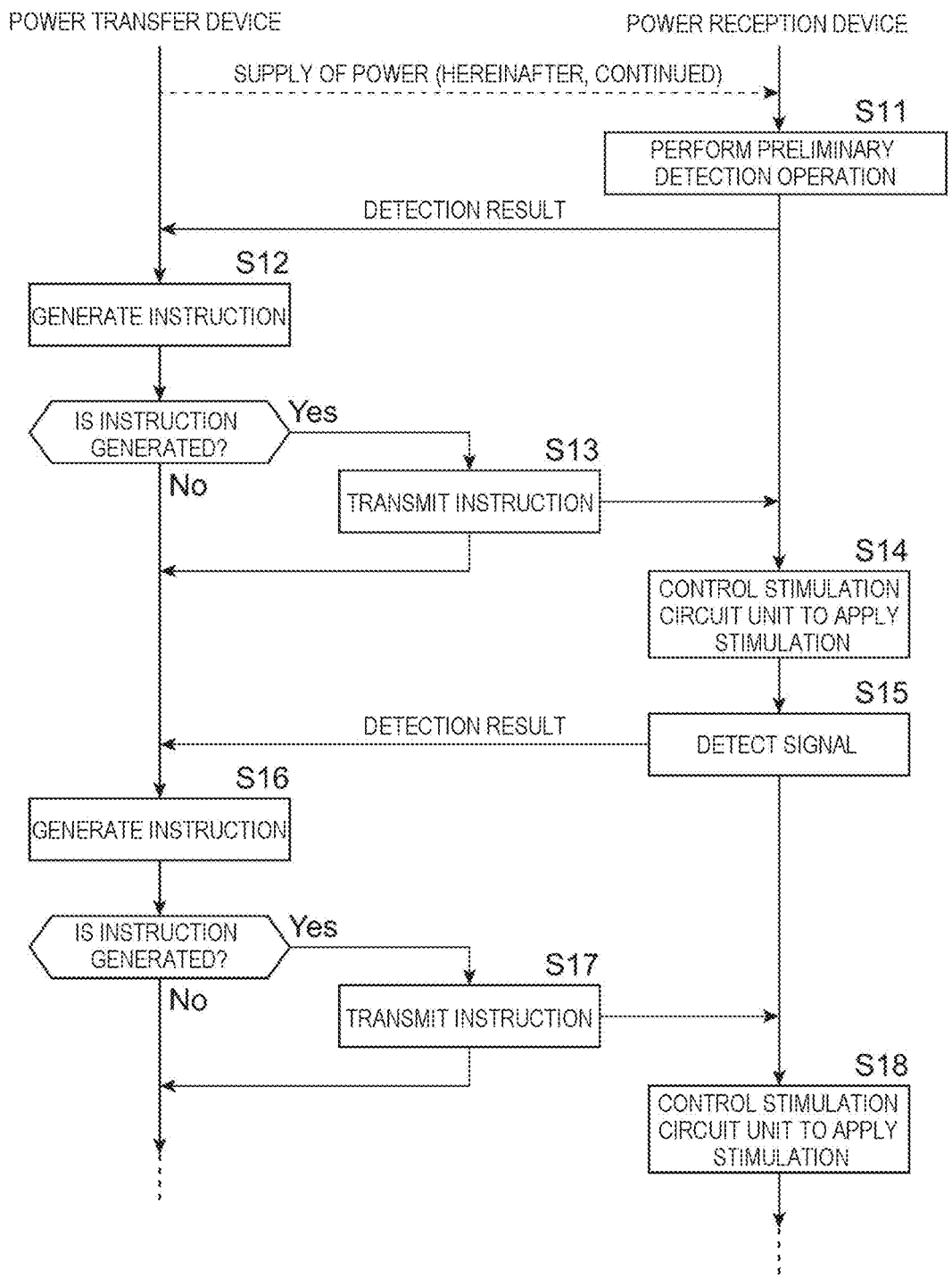
FIG. 17 is another flowchart illustrating an operation example of a power transfer system according to the embodiment of the present invention.
Figure 18:
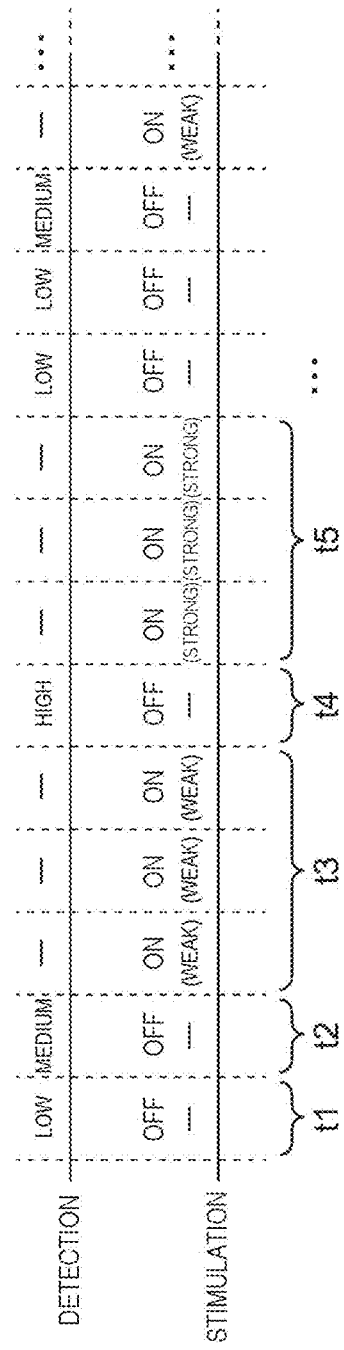
FIG. 18 is an explanatory diagram illustrating an operation example of a power transfer system according to the embodiment of the present invention.

For example, as illustrated in FIGS. 17 and 18, until the instruction is received from the information processing unit 14, the information processing unit 62 controls the detection unit 63 to detect an electrical signal at the second predetermined site. The information processing unit 62 transmits information indicating the signal detected by the detection unit 63 to the information processing unit 14 of the power transfer device 10 (S11: preliminary detection operation). As an example, the information processing unit 62 generates information obtained by classifying the degree of a response (for example, which is determined based on the maximum amplitude of the signal, and hereinafter, referred to as degree of reaction) based on a signal (signal temporally varying in general) detected by the detection unit 63 within a time of a predetermined time (for example, five seconds) into any one of three stages of "low", "medium", and "high", and transmits the information to the information processing unit 14. Note that, in this example, the classification into each stage may be determined by setting in advance a lower limit threshold of the degree of reaction to be determined as each stage and determining whether or not a value exceeds the lower limit threshold of each stage.

The information processing unit 14 receives information indicating a signal detected by the detection unit 63 of the power reception device 20 from the information processing unit 62, and generates an instruction for controlling the stimulation circuit unit 61 of the power reception device 20 as necessary on the basis of the information (S12).

As an example, the information processing unit 14 generates an instruction to apply a stimulation of a predetermined mode for 15 seconds when the degree of reaction indicated by the most recently received information is "medium" or "high". For example, in a period t1 in FIG. 18, since the degree of reaction indicated by the received information is "low", the information processing unit 14 does not generate an instruction to apply stimulation. Therefore, no stimulation is applied after this period (in FIG. 18, a period in which no stimulation is applied is indicated as "OFF". The information processing unit 62 acquires a detection result obtained by the detection unit 63 in the period in which no stimulation is applied.).

On the other hand, since the degree of reaction indicated by the information received in a period t2 of FIG. 18 is "medium", the information processing unit 14 generates an instruction to apply stimulation of a predetermined mode for 15 seconds. When generating the instruction, the information processing unit 14 transmits the instruction to the information processing unit 62 (S13).

The information processing unit 62 receives the instruction transmitted by the information processing unit 14, and controls the stimulation circuit unit 61 in a mode indicated by the instruction (S14).

Accordingly, as illustrated in FIG. 18, the stimulation is applied over a period t3 (15 seconds) after the period t2 (in FIG. 18, it is indicated as the stimulation "ON").

Moreover, after the control for the stimulation circuit unit 61 is ended, the information processing unit 62 transmits information indicating the signal detected by the detection unit 63 to the information processing unit 14 of the power transfer device 10 (S15, for example, a period t4 in FIG. 18, and the like).

The information processing unit 14 receives information indicating the signal detected by the detection unit 63 of the power reception device 20 from the information processing unit 62, and generates an instruction for controlling the stimulation circuit unit 61 of the power reception device 20 on the basis of the information (S16), and transmits the generated instruction (S17). The information processing unit 62 receives the instruction transmitted from the information processing unit 14, and controls the stimulation circuit unit 61 in a mode indicated by the instruction (S18, for example, a period t5 in FIG. 18, and the like)

Hereinafter, the information processing units 14 and 62 repeatedly execute the processing of Steps S15 to S18.

Note that, here, the stimulation application mode included in the instruction generated by the information processing unit 14 includes amplitude and a frequency in addition to the duration of the applied electrical stimulation. For example, when generating an instruction in Step S13 or Step S16, the information processing unit 14 determines whether or not to apply electrical stimulation (timing to apply electrical stimulation) on the basis of the information indicating a signal most recently detected by the detection unit 63 and received from the information processing unit 14 immediately before, and when it is determined to apply the electrical stimulation, the information processing unit 14 determines parameters of the stimulation application, such the amplitude and the frequency in addition to the duration of the applied electrical stimulation.

Accordingly, for example, the information processing unit 14 can perform control so as to make the amplitude (illustrated as "strong" in FIG. 18) of the electrical stimulation applied when the degree of reaction is "high" greater than the amplitude (illustrated as "weak" in FIG. 18) of the electrical stimulation applied when the degree of reaction detected by the power reception device 20 immediately before is "medium", or make the frequency of the electrical stimulation applied when the degree of reaction is "high" higher than the frequency of the electrical stimulation applied when the degree of reaction detected by the power reception device 20 immediately before is "medium".

Note that the administrator may control the information processing unit 14 in advance so as to artificially set a stimulation application mode for the information transmitted by the power reception device 20.

[Selection of Electrode Position]

Figure 15B:
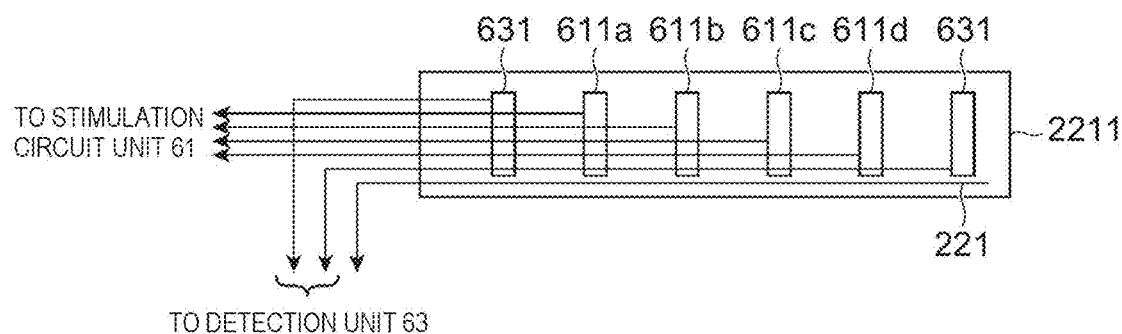

Furthermore, as illustrated in FIG. 15A, the number of the stimulation electrodes 611 disposed on the extension wiring element 2211 is not necessarily two. When the number of the stimulation electrodes 611 is two or more, the stimulation only needs to be applied by selecting two electrodes among two or more electrodes. For example, FIG. 15B illustrates an example in which four stimulation electrodes are disposed between the electrodes of a pair of the sensors 631, and each of the stimulation electrodes is electrically connected to the stimulation circuit unit 61 through the wiring formed on the extension wiring element 2211. Also in this example, the electrodes may be disposed at a predetermined distance (for example, 2 mm) or more so as not to be short-circuited to each other (except for the electrode having the common potential).

In this example, the stimulation application mode may include designation that which electrode is used for stimulation application. For example, the information processing unit 14 may instruct the information processing unit 62 to use an electrode 611*a* and an electrode 611*d* which are illustrated in FIG. 15B respectively as a positive electrode and a negative electrode, at the time of applying the stimulation, as one of the parameters indicating the stimulation application mode. In this case, the information processing unit 62 controls the stimulation circuit unit 61 to change the potential between the electrode 611*a* and the electrode 611*d* with an amplitude and a frequency separately designated by parameters. Furthermore, at this time, electrodes 611*b* and 611*c* are not controlled (no potential difference is generated). Furthermore, in another case, the information processing unit 14 may instruct the information processing unit 62 to use the electrode 611*b* and the electrode 611*c* which are illustrated in FIG. 15B respectively as a positive electrode and a negative electrode, at the time of applying the stimulation, as one of the parameters indicating the stimulation application mode. In this case, the information processing unit 62 controls the stimulation circuit unit 61 to change the potential between the electrode 611*b* and the electrode 611*c* with an amplitude and a frequency separately designated by parameters. At this time, the electrodes 611*a* and 611*d* are not controlled (no potential difference is generated).

Furthermore, in this example, one of the electrodes of a pair of the sensors 631 may be selectively set as GND and the other one of the electrodes of a pair of the sensors 631 is selectively set as a sensing electrode (electrode to be turned on; the sensor 631 of this example detects an electrical signal based on a potential difference between the sensing electrode and the GND electrode).

[Another Operation in Power Reception Device]

Here, in the example of FIG. 17, the preliminary detection operation illustrated in Step S11 is not necessarily required. For example, the user may input, to the information processing unit 14 of the power transfer device 10, an instruction to be transmitted to the information processing unit 62 of the power reception device 20, regardless of the detection result of the preliminary detection operation. In this example, in Step S13 of FIG. 17, the information processing unit 14 transmits the instruction input from the user to the information processing unit 62.

Furthermore, this instruction may be a program that causes the information processing unit 62 to perform an operation by predetermined condition branching. For example, this instruction is input via a personal computer communicably connected to the power transfer device 10, a tablet terminal, a mobile terminal including a smartphone, or the like. In the example of the present embodiment, this instruction is input through a screen illustrated in FIG. 19.

On this screen, an example (A) of the signal detected by the detection unit 63, which is transmitted by the information processing unit 62 in the past and received by the information processing unit 14, is displayed in time series. Moreover, in this signal, information indicating the magnitude of the stimulation applied in the past in a period in which the stimulation was applied may be displayed (T).

Furthermore, an input field for inputting an instruction is displayed on this screen (B). In this input field, a date, identification information (Trial Number) for specifying an instruction, a length of a period during which an instruction is to be executed (Treatment Duration), an instruction execution mode (for example, a mode indicating whether to be executed while communicating with the information processing unit 14 or whether to be autonomously executed by the information processing unit 62 as in the following example), and the like can be input.

Furthermore, the input field (B) includes an input field of information (b1) as a determination criterion of the degree of reaction and information (b2) of setting of stimulation to be applied. Specifically, in the example of FIG. 19, conditions for a frequency (f) and amplitude (v) of the signal detected by the detection unit 63 are described corresponding to each degree of reaction (in the example of FIG. 19, determination criteria corresponding to the degrees of reaction of "medium" and "high" are shown) as the determination criterion of the degree of reaction based on the detection result of the detection unit 63. In this condition, for example, "medium" is set when a frequency (for this purpose, the detection unit 63 includes a circuit that detects the frequency of a signal) of a signal detected by the detection unit 63 ranges from 100 Hz to 500 Hz and an amplitude is equal to or less than 100 μV, and "high" is set when a frequency (for this purpose, the detection unit 63 includes a circuit that detects the frequency of a signal) of a signal detected by the detection unit 63 ranges from 230 Hz to 500 Hz and an amplitude is equal to or less than 200 μV.

In the information (b2) of setting stimulation of the input field, a time (t) for applying stimulation, an amplitude (a) of the stimulation to be applied, a frequency (fs) of the stimulation to be applied, a pulse width (pw), and the like can be set. Note that in the example of FIG. 19, one type of stimulation is set, but as described above, different types of stimulation may be set according to the degree of reaction for the detected signal.

Moreover, on this screen, it may be possible to perform setting of an electrode position for applying stimulation, and it may be possible to perform setting of exchanging the positions of the GND of the sensor and the electrode of the sensor which is turned on (C).

That is, an example of the instruction set on this screen is an instruction autonomously executed by the information processing unit 62. The instruction is as follows:

When the degree of reaction based on the detection result in the detection unit 63 is "low", nothing is performed;

When the degree of reaction based on the detection result in the detection unit 63 is "medium", stimulation with a frequency fs and an amplitude a is applied only for a time t; and Even when the degree of reaction based on the detection result in the detection unit 63 is "high", the stimulation with the frequency fs and the amplitude a is applied only for the time t. As described above, condition branching may be performed according to the degree of reaction, and stimulations with different frequencies, amplitudes, and times may be applied. However, here, it is described that the above-described instruction is transmitted from the information processing unit 14.

In this example, the information processing unit 62 receives and stores the instruction transmitted by the information processing unit 14 in Step S14. The information processing unit 62 controls the stimulation circuit unit 61 in a predetermined mode according to the received instruction.

Therefore, also in this example, as illustrated in FIG. 18, the stimulation is applied over a period t3 (15 seconds) after the period t2.

In Step S15, after the control for the stimulation circuit unit 61 ends, the information processing unit 62 acquires information indicating the signal detected by the detection unit 63. In this example, without transmitting the acquired information to the information processing unit 14 of the power transfer device 10 (skipping Steps S16 and S17), the processing of Step S18 is executed, an instruction for controlling the stimulation circuit unit 61 is generated according to the instruction received from the information processing unit 14, and the stimulation circuit unit 61 is controlled in a mode indicated by the generated instruction (for example, a period t5 in FIG. 18).

Hereinafter, the information processing unit 62 repeatedly executes the processing of Steps S15 and S18. Furthermore, when the instruction transmitted by the information processing unit 14 in Step S14 includes information regarding a length of a period in which the instruction is to be executed, the information processing unit 62 may stop the processing when the period has elapsed from the start of the processing.

Furthermore, in this example, when the power reception device 20 incorporates a battery, the power transfer device 10 may not necessarily be disposed in a range in which communication and power supply can be performed. Furthermore, when the power reception device 20 does not incorporate the battery, the power transfer device 10 may continue to supply power to the power reception device 20 in the period of the above-described processing.

[Application of Test Stimulation]

Furthermore, in this example, the information processing unit 14 determines an application mode of stimulation to be applied by the power reception device 20 on the basis of the latest signal detected by the power reception device 20, but the present embodiment is not limited to this example.

For example, the information processing unit 62 of the power reception device 20 may control the stimulation circuit unit 61 to apply stimulations in a plurality of stimulation modes different from each other, and may control the detection unit 63 to detect a predetermined electrical signal at the second predetermined site of the human body at each timing after the stimulations are applied in the stimulation modes different from each other, and may transmit the signal indicating a result of the detection to the information processing unit 14 of the power transfer device 10.

In this example, since responses to the stimulations in the stimulation modes different from each other are detected and the information is provided, the information processing unit 14 can provide the information for subsequent determination of the stimulation mode. As an example, this information is presented to the administrator, and is provided as a reference when the administrator artificially sets a stimulation application mode for the information transmitted by the power reception device 20.

[Autonomous Operation of Power Reception Device]

Furthermore, in the above description of the operation example, the power transfer device 10 determines the stimulation application mode on the basis of the signal detected by the power reception device 20 and controls the power reception device 20, but the present embodiment is not limited to this.

For example, power may be supplied from the power transfer device 10 to charge a rechargeable battery included in the power reception device 20, and a program for controlling the stimulation application mode executed by the information processing unit 62 may be transmitted from the power transfer device 10. The information processing unit 62 according to the program determines a stimulation application mode according to a condition determined in the program on the basis of the information indicating the signal output by the detection unit 63, and controls the stimulation circuit unit 61 so as to apply the stimulation in the determined application mode. Here, the stimulation application mode includes the duration, intensity (amplitude), frequency, and the like of the stimulation, and also includes information indicating which electrode is the positive electrode, which electrode is the negative electrode, and to which the stimulation is applied in a case where there are three or more electrodes for applying the stimulation. In this example, it is not necessary to attach the power transfer device 10 to a portion other than the human body, and the stimulation illustrated in FIG. 18 is applied by the autonomous operation of the power reception device 20.

[Example of Arrangement on Human Body]

As described above, in the power transfer device 10 and the power reception device 20 of the present embodiment, the power reception device 20 is embedded (implanted) at a position of, for example, about 1 cm to 2 cm subcutaneously in the human body. Furthermore, the power transfer device 10 is disposed on the surface of the human body at a position at which power can be supplied to the power reception device 20. The position of the power reception device 20 can be confirmed by touching a human body surface.

Figure 20A:
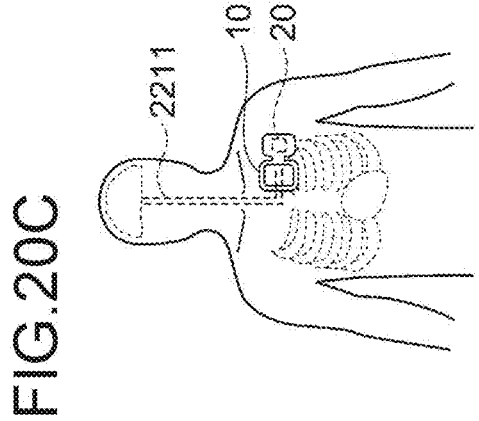
FIGS. 20A-20E are explanatory diagrams illustrating an arrangement example of each unit of a power transfer system according to the embodiment of the present invention.
Figure 20B:
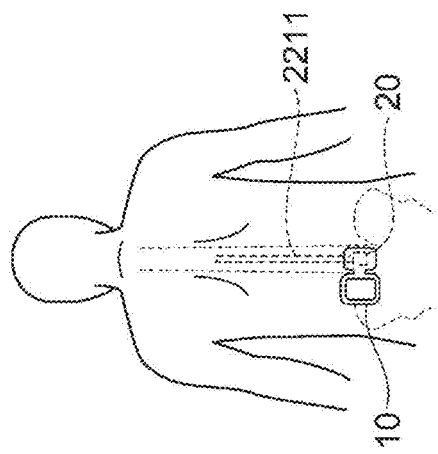

This specific arrangement may be selected according to the purpose. For example, as illustrated in FIGS. 20(a) and 20(b), the power reception device 20 may be disposed on the back side and the pelvis of the human body, the power transfer device 10 may be disposed at a position (on the surface of the human body) to which power can be supplied, and the stimulation electrode 611 and the electrode of the sensor 613 which are disposed on the extension wiring element 2211 and the like may be extended to the sacrum (FIG. 20A) or may be disposed on the spinal cord (FIG. 20B).

Figure 20C:
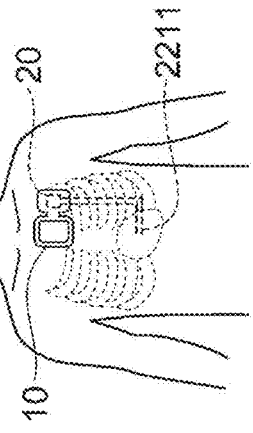
Figure 20D:
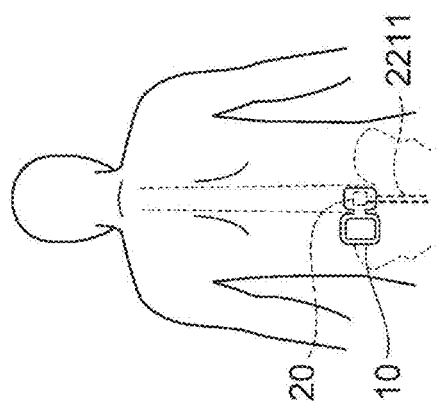
Figure 20E:
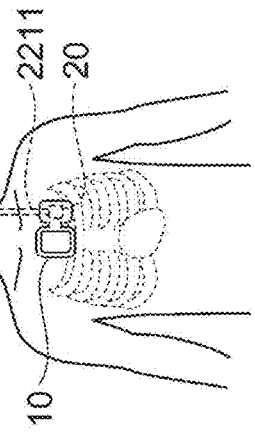

Furthermore, the power transfer device 10 and the power reception device 20 may be disposed on the front side (side facing the face) of the human body. In this case, for example, the power reception device 20 may be disposed on a rib, the power transfer device 10 may be disposed at a position (on the surface of the human body) to which power can be supplied, and the stimulation electrode 611 and the electrode of the sensor 613 which are disposed on the extension wiring element 2211 and the like may be extended to the brain (FIG. 20C), a vagal nerve of a neck (FIG. 20D), or the myocardium (FIG. 20E) as already illustrated.

Figure 21:
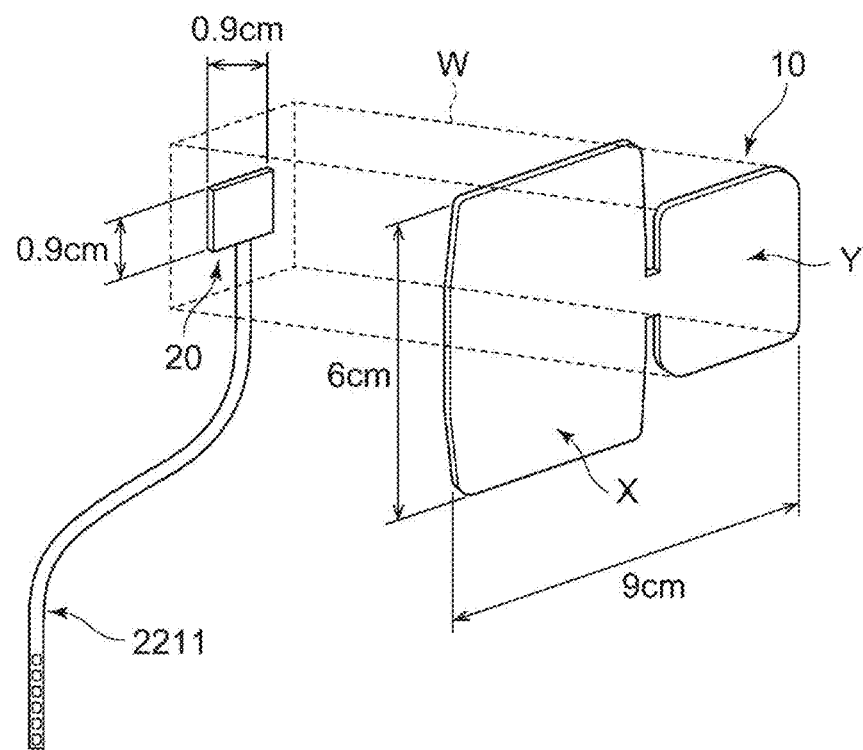
FIG. 21 is an explanatory diagram illustrating a shape example of each unit of a power transfer system according to the embodiment of the present invention.
Figure 22:
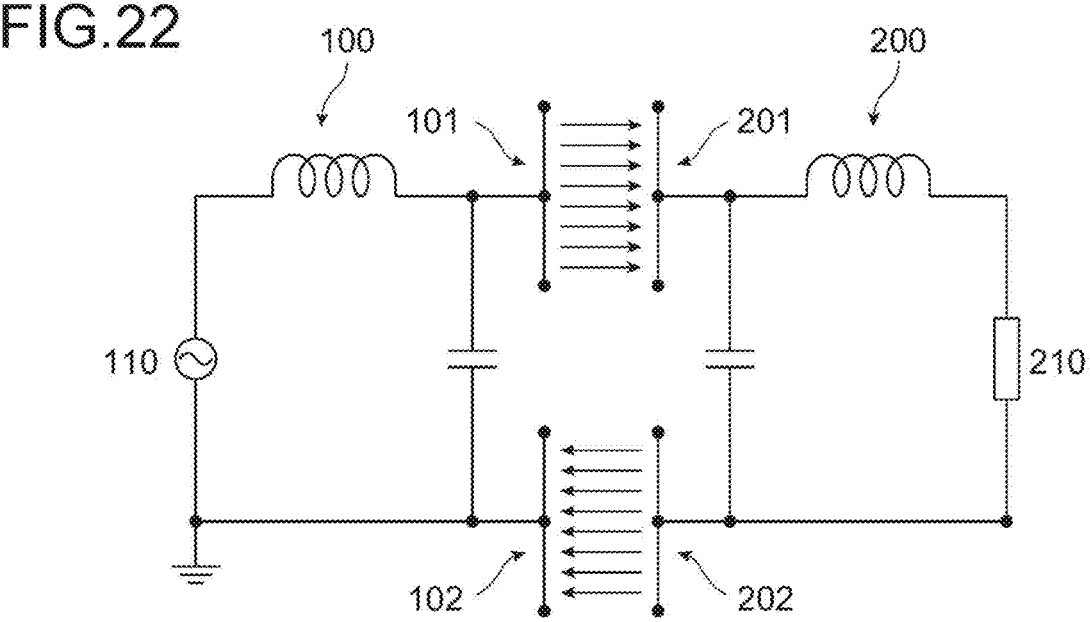
FIG. 22 is a schematic circuit diagram illustrating an example of a power transfer system of the related art.

For example, the power reception device 20 in these examples may have a size to an extent of forming a rectangular plate shape having one side of about 1 cm and a thickness of about 0.3 cm. Furthermore, as illustrated in FIG. 21, the power transfer device 10 may have a shape formed by connecting a rectangular main body portion (X) including the AC power source unit 11 and the power transfer-side compensation circuit 12 and a rectangular power transfer element portion (Y) including the power transfer element. Therefore, in this example, a trajectory (W) obtained by moving the surface of the power transfer element portion (Y) in the normal direction forms the overlap region.

The ratios of the size, length and width, and thickness are merely examples, and in the device and the like of the present embodiment, the ratios of the size, length and width, and thickness may be different values.

[Example other than Human Body]

Furthermore, in the above-described example, the power reception device 20 may be disposed, for example, inside a human body (in the body of a human which is an example of an animal), but the power reception device 20 may be disposed inside the body of the animal other than the human.

EXAMPLE

An experimental example of power transfer using the power transfer system 1 having the above-described configuration will be described below. In the following example, a case where the power transfer element and the power reception element are the power transfer plate 13 and the power reception plate 21, respectively, is taken as an example.

Hereinafter, an example in which power is transferred using the power transfer device 10 including the power transfer-side compensation circuit 12 of FIG. 2B and the power reception device 20 including the output circuit 23' including the power reception-side compensation circuit 22 illustrated in FIG. 3B and the rectifier circuit unit 23'x will be described.

Figure 7:
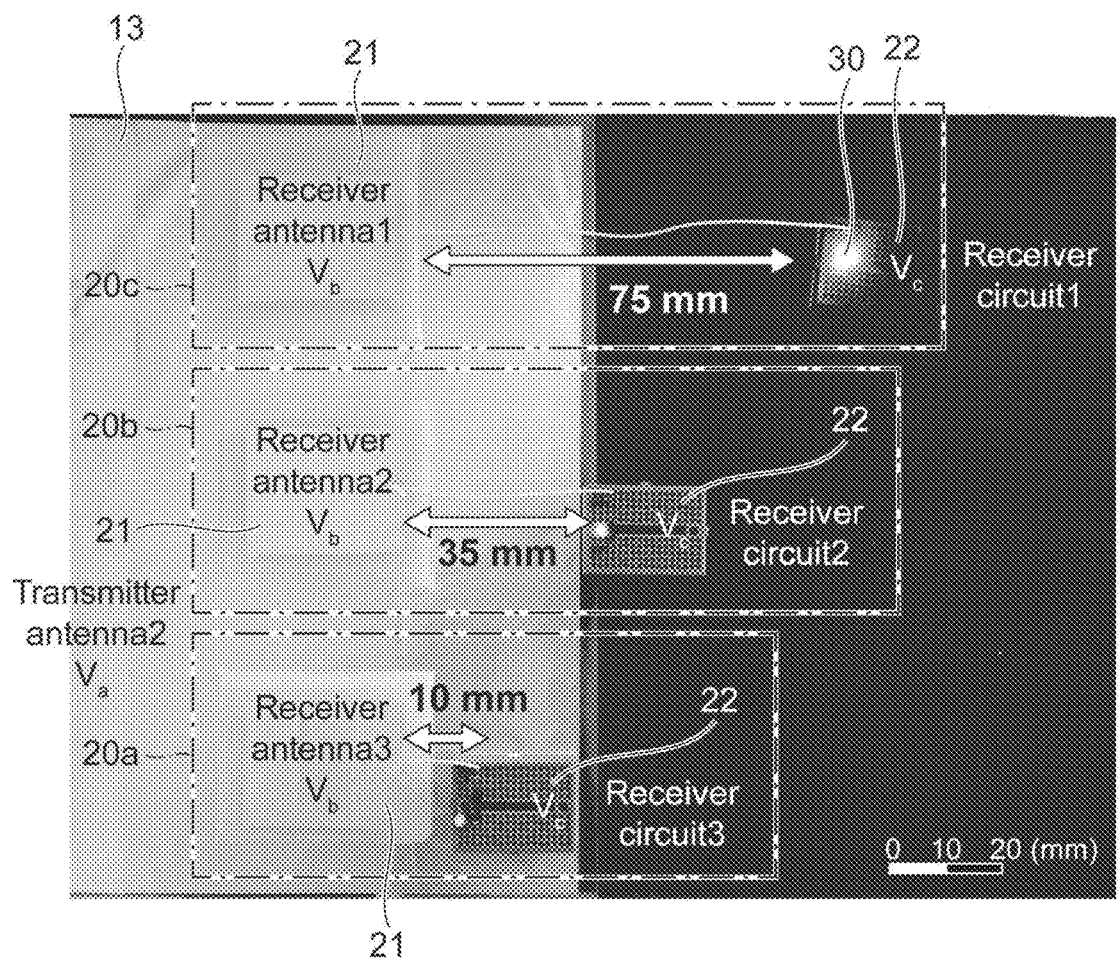
FIG. 7 is an explanatory diagram illustrating an example of a power transfer system according to the embodiment of the present invention.

FIG. 7 illustrates an example in which three power reception devices 20 are disposed to receive power from one power transfer plate 13. In each of the power reception devices 20 (hereinafter, it is referred to as the power reception devices 20a, 20b, and 20c for distinction), the power reception-side compensation circuits 22 are disposed at positions separated from the power reception plate 21 by 10 mm (power reception device 20a), 35 mm (power reception device 20b), and 75 mm (power reception device 20c), respectively. However, in the power reception device 20a, both the power reception plate 21 and the power reception-side compensation circuit 22 are disposed such that the distances from the power transfer plate 13 do not vary.

Furthermore, in the power reception device 20b, the distance between the power transfer plate 13 and the power reception plate 21 is the same as that from the power reception device 20a, and the power reception-side compensation circuit 22 is disposed outside the power transfer plate 13 and at a position adjacent to the edge of the power transfer plate 13.

In the power reception device 20c, the distance between the power transfer plate 13 and the power reception plate 21 is the same as that from the power reception devices 20a and 20b, and the power reception-side compensation circuit 22 is disposed further outside the power transfer plate 13 and at a position separated from the edge of the power transfer plate 13 by about 40 mm. Furthermore, an LED as the load was connected to any of the power reception devices 20a, 20b, and 20c.

In the example of FIG. 7, the LEDs connected to the power reception device 20a and 20b are not turned on, but the LED connected to the power reception device 20c is turned on.

This indicates that the power is transferred in a case where the intensity of the electric field formed by the power transfer plate 13 is different between a position at which the power reception plate 21 is disposed and a position at which (at least a part of) the power reception-side compensation circuit 22 is disposed.

Furthermore, a power transfer example when the position of the power reception-side compensation circuit 22 is set at a position greater, by 10 mm, than the distance between the power transfer plate 13 and the power reception plate 21 from the power transfer plate 13 will be described with reference to FIG. 8.

Figure 8:
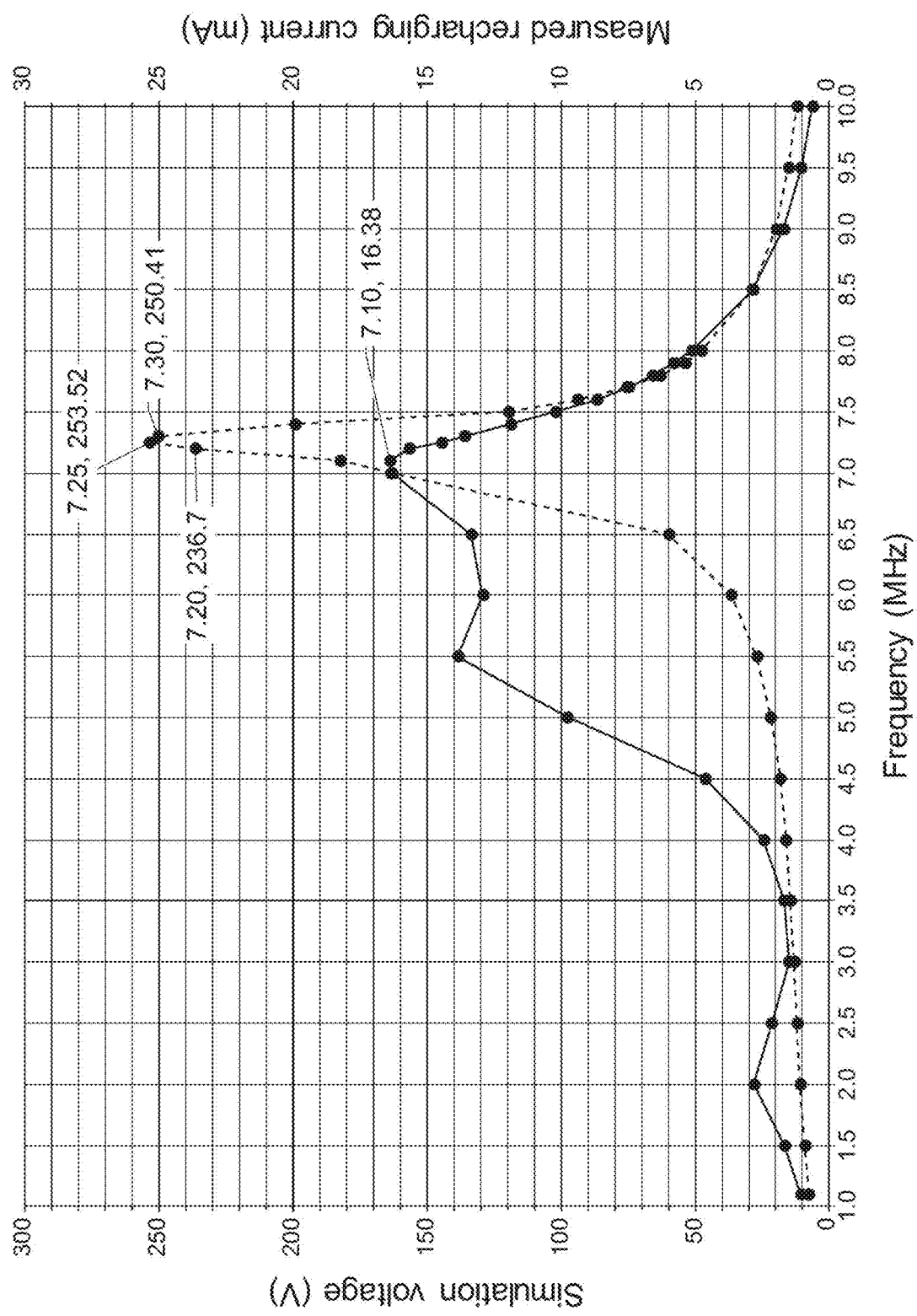
FIG. 8 is an explanatory diagram illustrating an example of a change in power transfer efficiency of a power transfer system according to the embodiment of the present invention.

FIG. 8 illustrates an example in which the change in a current supplied to the load 30 by the power reception device is measured while changing the frequency of the AC power generated by the AC power source unit 11 of the power transfer device 10. In this example, the maximum current amount (16 mA) is obtained in the vicinity of the frequency of 7 MHz, but it is illustrated that the current amount supplied to the load 30 is less than 1 mA in a case where the frequency is, for example, about 10 MHz.

Figure 9:
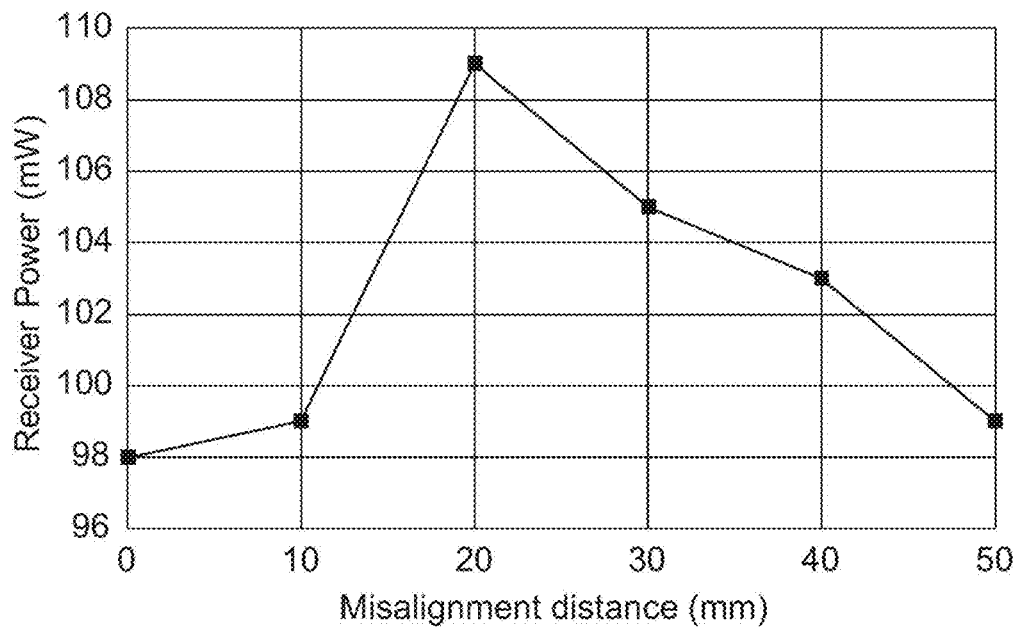
FIG. 9 is an explanatory diagram illustrating another example of a change in power transfer efficiency of a power transfer system according to the embodiment of the present invention.

Moreover, FIG. 9 illustrates an example in which the change in the current supplied to the load 30 by the power reception device 20 is measured when the alignment (deviation between the centers) between the power transfer plate 13 and the power reception plate 21 is changed.

As illustrated in FIG. 9, the amount of current supplied to the load 30 peaks when the centers of the power transfer plate 13 and the power reception plate 21 are deviated from each other by about 20 mm. However, it is understood that there is only a difference of about 10% in the amount of current supplied to the load 30 as compared with a case where there is no deviation of the centers from each other.

The invention claimed is:

1. A power transfer system comprising a power transfer device and a power reception device which wirelessly transmit and receive power, respectively,
wherein the power transfer device includes
an AC power source unit, and
a single power transfer element connected to the AC power source unit,
the power reception device includes
a single power reception element electrically coupled to the power transfer element of the power transfer device, and
a power reception circuit connected to the power reception element and outputting power, and
the power reception circuit includes a different potential field that is disposed at a position that is an electric field formed by the power transfer element and at which intensity of the electric field is different from intensity of an electric field formed at a position of the power reception element.

2. The power transfer system according to claim 1,
wherein each of the power transfer element and the power reception element has a plate shape, and
the power reception plate is capacitively coupled to the power transfer plate.

3. The power transfer system according to claim 1,
wherein the power transfer element is an element obtained by molding a conductor into a first predetermined shape, and
the power reception element is an element obtained by molding the conductor into a second predetermined shape.

4. The power transfer system according to claim 3,
wherein the first predetermined shape of the power transfer element is a coil shape of which one end is connected to the AC power source unit and the other end is open, and
the second predetermined shape of the power reception element is a coil shape of which one end is connected to the power reception circuit and the other end is open.

5. The power transfer system according to claim 3,
wherein the first predetermined shape of the power transfer element is a coil shape of which one end is connected to the AC power source unit and the other end is open, and
the second predetermined shape of the power reception element is a coil shape of which both ends are connected to the power reception circuit.

6. The power transfer system according to claim 3,
wherein the first predetermined shape of the power transfer element is a coil shape of which both ends are connected to the AC power source unit, and
the second predetermined shape of the power reception element is a coil shape of which both ends are connected to the power reception circuit.

7. The power transfer system according to claim 1,
wherein the power transfer device further includes a first information processing unit,
the power reception device includes a second information processing unit, and
the first information processing unit and the second information processing unit transmit and receive information by using the power transfer element and the power reception element.

8. The power transfer system according to claim 1,
wherein the power reception device is embedded inside a human body or an animal body other than the human body.

9. The power transfer system according to claim 8,
wherein the power transfer device is disposed outside the human body or the animal body other than the human body, inside which the power reception device is disposed,
the power reception device further includes
a stimulation application unit that is controlled by the second information processing unit and applies electrical stimulation to a first predetermined site inside the animal body, and
a detection unit that detects a predetermined electrical signal at a second predetermined site inside the animal body and outputs a detection result to the second information processing unit,
the second information processing unit transmits, to the first information processing unit of the power transfer device, a signal indicating the detection result input from the detection unit, and
the first information processing unit of the power transfer device determines a stimulation application mode of the stimulation application unit on a basis of the signal received from the second information processing unit of the power reception device, and transmits, to the second information processing device, a signal for controlling the stimulation application unit to apply stimulation in the application mode.

10. The power transfer system according to claim 9,
wherein the second information processing unit controls the detection unit to detect the predetermined electrical signal at the second predetermined site inside the animal body until the signal related to the stimulation application mode of the stimulation application unit is received from the first information processing unit, and transmits a signal indicating a detection result to the first information processing unit of the power transfer device.

11. The power transfer system according to claim 9, wherein
the second information processing unit controls the detection unit to detect the predetermined electrical signal at the second predetermined site inside the animal body after stimulation is applied by the stimulation application unit, and transmits a signal indicating a detection result to the first information processing unit of the power transfer device.

12. The power transfer system according to claim 11,
wherein the second information processing unit controls the detection unit to detect the predetermined electrical signal at the second predetermined site inside the animal body at each timing after the stimulation is applied by the stimulation application unit in application modes different from each other, and transmits a signal indicating a detection result to the first information processing unit of the power transfer device.

13. The power transfer system according to claim 9,
wherein the first predetermined site is a site of a predetermined nerve inside the animal body.

14. The power transfer system according to claim 9, further comprising, as the different potential field of the power reception device:
a plurality of electrodes that is connected to the stimulation application unit and disposed at the first predetermined site to apply electrical stimulation to the first predetermined site; and a plurality of electrodes that is connected to the detection unit and disposed at the second predetermined site to detect a predetermined electrical signal at the second predetermined site.

15. The power transfer system according to claim 1, wherein the different potential field is disposed at a position separated from the power transfer element by at least equal to or greater than 10 mm as compared with a distance between the power transfer element and the power reception element.

16. The power transfer system according to claim 1, wherein the power reception circuit a further includes rectifier circuit unit that rectifies an alternating current flowing in from the power reception element, and supplies a current rectified by the rectifier circuit unit to a load.

17. The power transfer system according to claim 1, wherein the power reception circuit is disposed at a position that is an electric field formed by the power transfer element and at which intensity of the electric field is different from intensity of an electric field formed at a position of the power reception element.

18. The power transfer system according to claim 1, wherein the power reception circuit is connected to a wiring on which an end of the power reception circuit as a different potential field is disposed at a position that is an electric field formed by the power transfer element and at which intensity of the electric field is different from intensity of an electric field formed at a position of the power reception element.

19. A power transfer device that wirelessly transfers power to a power reception device including a power reception element and a power reception circuit, the power transfer device comprising:

an AC power source unit; and
a single power transfer element that is connected to the AC power source unit,
wherein electric fields with intensities different from each other are formed at positions at which the power reception element and the power reception circuit are respectively disposed.

20. A power reception device that wirelessly receives power from a power transfer device,
wherein the power transfer device includes an AC power source unit, and a single power transfer element connected to the AC power source unit,
the power reception device includes
a single power reception element electrically coupled to the power transfer element of the power transfer device, and
a power reception circuit connected to the power reception element and outputting power, and
the power reception circuit includes a different potential field that is disposed at a position that is an electric field formed by the power transfer element and at which intensity of the electric field is different from intensity of an electric field formed at a position of the power reception element.

21. A wireless power transfer method using a power transfer device including an AC power source unit and a single power transfer element connected to the AC power source unit, and a power reception device including a single power reception element electrically coupled to the power transfer element of the power transfer device and a power reception circuit connected to the power reception element and outputting power, the method comprising driving a power source of the AC power source unit such that the power transfer element forms electric fields having different intensities at positions at which the and the power reception circuit are power reception element respectively disposed.

* * * * *